US011393561B2

(12) United States Patent
Chou

(10) Patent No.: US 11,393,561 B2
(45) Date of Patent: Jul. 19, 2022

(54) DEVICES AND METHODS FOR AUTHENTICATING A MEDICAL TEST AND USE OF THE SAME

(71) Applicant: Essenlix Corporation, Monmouth Junction, NJ (US)

(72) Inventor: Stephen Y. Chou, Princeton, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

(21) Appl. No.: 16/755,825

(22) PCT Filed: Oct. 12, 2018

(86) PCT No.: PCT/US2018/055731
§ 371 (c)(1),
(2) Date: Apr. 13, 2020

(87) PCT Pub. No.: WO2019/075415
PCT Pub. Date: Apr. 18, 2019

(65) Prior Publication Data
US 2020/0303044 A1    Sep. 24, 2020

Related U.S. Application Data

(60) Provisional application No. 62/572,121, filed on Oct. 13, 2017.

(51) Int. Cl.
*G16H 10/40*    (2018.01)
*A61B 5/1171*   (2016.01)
(Continued)

(52) U.S. Cl.
CPC ........... *G16H 10/40* (2018.01); *A61B 5/1171* (2016.02); *A61B 5/1172* (2013.01);
(Continued)

(58) Field of Classification Search
CPC ........ G16H 10/40; G16H 10/60; G16H 40/67; G16H 30/40; A61B 5/1171; A61B 5/1172;
(Continued)

(56) References Cited

U.S. PATENT DOCUMENTS 3,368,872 A    2/1968 Natelson
3,447,863 A    6/1969 Patterson
(Continued)

FOREIGN PATENT DOCUMENTS

AU    198813789 A    9/1988
AU       619459 B    1/1992
(Continued)

OTHER PUBLICATIONS

Van Vliet, Dillys et al., Prediction of asthma exacerbations in children by innovative exhaled inflammatory markers: Results of a longitudinal study, PLOS ONE, Mar. 23, 2015, vol. 10. No. 3, e0119434.
(Continued)

*Primary Examiner* — John B Strege

(57) ABSTRACT

Devices and methods for authenticating medical tests, such as a saliva test is provided. The devices can simultaneously image at least one biometric identifier associated with an intended subject being tested so as to provides authentication of a medical test such as a saliva test. The present invention has useful and practical utility in health monitoring, mobile monitoring, and crime monitoring in the fields of insurance, health, and medication.

19 Claims, 5 Drawing Sheets

(51) Int. Cl.

| | |
|---|---|
| *A61B 90/96* | (2016.01) |
| *G16H 40/67* | (2018.01) |
| *G16H 10/60* | (2018.01) |
| *A61B 5/1172* | (2016.01) |
| *A61B 10/00* | (2006.01) |
| *A61F 13/38* | (2006.01) |
| *B01L 3/00* | (2006.01) |
| *G01N 35/00* | (2006.01) |
| *G06K 7/10* | (2006.01) |
| *G06K 7/14* | (2006.01) |
| *G06K 19/06* | (2006.01) |
| *G06Q 40/08* | (2012.01) |
| *G06Q 50/26* | (2012.01) |
| *G06V 40/70* | (2022.01) |
| *G06V 40/16* | (2022.01) |
| *G06V 40/18* | (2022.01) |

(52) U.S. Cl.
CPC ........ *A61B 5/1176* (2013.01); *A61B 10/0051* (2013.01); *A61B 90/96* (2016.02); *A61F 13/38* (2013.01); *B01L 3/508* (2013.01); *G01N 35/00871* (2013.01); *G06K 7/10722* (2013.01); *G06K 7/1413* (2013.01); *G06K 7/1417* (2013.01); *G06K 19/06028* (2013.01); *G06K 19/06037* (2013.01); *G06Q 40/08* (2013.01); *G06Q 50/265* (2013.01); *G06V 40/172* (2022.01); *G06V 40/197* (2022.01); *G06V 40/70* (2022.01); *G16H 10/60* (2018.01); *G16H 40/67* (2018.01); *B01L 2300/0654* (2013.01); *B01L 2300/0816* (2013.01); *B01L 2300/168* (2013.01)

(58) Field of Classification Search
CPC ..... A61B 5/1176; A61B 5/08; A61B 5/14507; A61B 5/14532; A61B 5/14542; A61B 5/201; A61B 5/4076; A61B 5/411; A61B 5/4306; A61B 5/4842; A61B 90/96; A61B 10/0051; A61B 2576/00; A61F 13/38; B01L 3/508; B01L 2300/0654; B01L 2300/0816; B01L 2300/168; G01N 35/00871; G06K 7/10722; G06K 7/1413; G06K 7/1417; G06K 7/00288; G06K 7/00617; G06K 7/00892; G06K 19/06028; G06K 19/06037; G06Q 40/08; G06Q 50/265; Y02A 90/10
See application file for complete search history.

(56) References Cited

U.S. PATENT DOCUMENTS

| | | | |
|---|---|---|---|
| 3,895,661 | A | 7/1975 | Praglin et al. |
| 3,925,166 | A | 12/1975 | Blume |
| 3,992,158 | A | 11/1976 | Przybylowicz et al. |
| 4,022,521 | A | 5/1977 | Hall et al. |
| 4,066,412 | A | 1/1978 | Johnson et al. |
| 4,088,448 | A | 5/1978 | Lilja et al. |
| 4,171,866 | A | 10/1979 | Tolles |
| 4,233,029 | A | 11/1980 | Columbus |
| 4,255,384 | A | 3/1981 | Kitajima et al. |
| 4,258,001 | A | 3/1981 | Pierce et al. |
| 4,329,054 | A | 5/1982 | Bachalo |
| 4,402,614 | A | 9/1983 | Porath |
| 4,427,294 | A | 1/1984 | Pietro |
| 4,430,436 | A | 2/1984 | Koyama et al. |
| 4,596,695 | A | 6/1986 | Cottingham |
| 4,745,075 | A | 5/1988 | Hadfield et al. |
| 4,806,311 | A | 2/1989 | Greenquist |
| 4,883,642 | A | 11/1989 | Bisconte |
| 4,906,439 | A | 3/1990 | Grenner |
| 4,911,782 | A | 3/1990 | Brown |
| 4,950,455 | A | 8/1990 | Smith |
| 5,002,736 | A | 3/1991 | Babbitt et al. |
| 5,039,487 | A | 8/1991 | Smith |
| 5,096,836 | A | 3/1992 | Macho et al. |
| 5,122,284 | A | 6/1992 | Braynin et al. |
| 5,132,097 | A | 7/1992 | Van Deusen et al. |
| 5,169,601 | A | 12/1992 | Ohta et al. |
| 5,188,968 | A | 2/1993 | Kano et al. |
| 5,223,219 | A | 6/1993 | Subramanian et al. |
| 5,281,540 | A | 1/1994 | Merkh et al. |
| 5,306,467 | A | 4/1994 | Douglas-Hamilton et al. |
| 5,321,975 | A | 6/1994 | Wardlaw |
| 5,362,648 | A | 11/1994 | Koreyasu et al. |
| 5,413,732 | A | 5/1995 | Buhl et al. |
| 5,427,959 | A | 6/1995 | Nishimura et al. |
| 5,431,880 | A | 7/1995 | Kramer |
| 5,591,403 | A | 1/1997 | Gavin et al. |
| 5,623,415 | A | 4/1997 | O'Bryan et al. |
| 5,753,456 | A | 5/1998 | Naqui et al. |
| 5,768,407 | A | 6/1998 | Shen et al. |
| 5,858,648 | A | 1/1999 | Steel et al. |
| 5,879,628 | A | 3/1999 | Ridgeway et al. |
| 5,888,834 | A | 3/1999 | Ishikawa et al. |
| 5,939,326 | A | 8/1999 | Chupp et al. |
| 5,948,686 | A | 9/1999 | Wardlaw |
| 6,004,821 | A | 12/1999 | Levine et al. |
| 6,016,367 | A | 1/2000 | Benedetti et al. |
| 6,017,767 | A | 1/2000 | Chandler |
| 6,022,734 | A | 2/2000 | Wardlaw |
| 6,106,778 | A | 8/2000 | Oku et al. |
| 6,180,314 | B1 | 1/2001 | Berndt |
| 6,235,536 | B1 | 5/2001 | Wardlaw |
| 6,350,613 | B1 | 2/2002 | Wardlaw et al. |
| 6,358,475 | B1 | 3/2002 | Berndt |
| 6,429,027 | B1 | 8/2002 | Chee et al. |
| 6,503,760 | B2 | 1/2003 | Malmqvist et al. |
| 6,551,554 | B1 | 4/2003 | Vermeiden et al. |
| 6,623,701 | B1 | 9/2003 | Eichele et al. |
| 6,632,652 | B1 | 10/2003 | Austin et al. |
| 6,714,287 | B2 | 3/2004 | Berndt |
| 6,723,290 | B1 | 4/2004 | Wardlaw |
| 6,844,201 | B2 | 1/2005 | Malmqvist et al. |
| 6,866,823 | B2 | 3/2005 | Wardlaw |
| 6,869,570 | B2 | 3/2005 | Wardlaw |
| 6,893,850 | B2 | 5/2005 | Ostuni et al. |
| 6,921,514 | B1 | 7/2005 | Vetter et al. |
| 6,929,953 | B1 | 8/2005 | Wardlaw |
| 6,939,032 | B2 | 9/2005 | Cosby et al. |
| 7,101,341 | B2 | 9/2006 | Tsukashima et al. |
| 7,179,423 | B2 | 2/2007 | Bohm et al. |
| 7,282,367 | B2 | 10/2007 | Kawamura |
| 7,393,658 | B2 | 7/2008 | Carbonell et al. |
| 7,410,617 | B2 | 8/2008 | Sakamoto |
| 7,410,807 | B2 | 8/2008 | D'Aurora |
| 7,468,160 | B2 | 12/2008 | Thompson et al. |
| 7,510,841 | B2 | 3/2009 | Stuelpnagel et al. |
| 7,510,848 | B2 | 3/2009 | Hammond et al. |
| 7,547,424 | B2 | 6/2009 | Haab et al. |
| 7,731,901 | B2 | 6/2010 | Wardlaw |
| 7,738,094 | B2 | 6/2010 | Goldberg |
| 7,850,916 | B2 | 12/2010 | Wardlaw |
| 7,862,773 | B2 | 1/2011 | Ibrahim |
| 7,863,411 | B2 | 1/2011 | Hammond et al. |
| 7,897,376 | B2 | 3/2011 | Porter et al. |
| 7,901,897 | B2 | 3/2011 | Stuelpnagel et al. |
| 7,903,241 | B2 | 3/2011 | Wardlaw et al. |
| 7,929,121 | B2 | 4/2011 | Wardlaw et al. |
| 7,929,122 | B2 | 4/2011 | Wardlaw et al. |
| 7,943,093 | B2 | 5/2011 | Adrien et al. |
| 7,951,599 | B2 | 5/2011 | Levine et al. |
| 7,995,194 | B2 | 8/2011 | Wardlaw et al. |
| 8,045,165 | B2 | 10/2011 | Wardlaw et al. |
| 8,058,073 | B2 | 11/2011 | Chiapperi et al. |
| 8,077,296 | B2 | 12/2011 | Wardlaw et al. |
| 8,081,303 | B2 | 12/2011 | Levine et al. |
| 8,133,738 | B2 | 3/2012 | Levine et al. |
| 8,158,434 | B2 | 4/2012 | Wardlaw |
| 8,221,985 | B2 | 7/2012 | Wardlaw et al. |

(56) References Cited

U.S. PATENT DOCUMENTS

| | | |
|---|---|---|
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 9,811,818 B1* | 11/2017 | Xing .................. G06Q 30/0226 |
| 10,783,225 B1* | 9/2020 | Collins .................. G16H 50/20 |
| 2001/0055882 A1 | 12/2001 | Ostuni |
| 2002/0164820 A1 | 11/2002 | Brown |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2004/0131345 A1 | 7/2004 | Kylberg et al. |
| 2004/0156755 A1 | 8/2004 | Levine |
| 2004/0214310 A1 | 10/2004 | Parker et al. |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0144454 A1* | 6/2011 | Koester .................. A61B 3/112 600/301 |
| 2011/0153362 A1* | 6/2011 | Valin .................. G06Q 20/105 705/3 |
| 2011/0206557 A1 | 8/2011 | Phan et al. |
| 2011/0212462 A1 | 9/2011 | Duffy et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2012/0321518 A1 | 12/2012 | Ermantraut et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0209332 A1 | 8/2013 | Wardlaw |
| 2013/0265054 A1 | 10/2013 | Lowery et al. |
| 2013/0309679 A1 | 11/2013 | Ismagilov et al. |
| 2014/0315242 A1 | 10/2014 | Rodriguez et al. |
| 2014/0368631 A1 | 12/2014 | Wardlaw et al. |
| 2014/0378320 A1 | 12/2014 | Hoffmann et al. |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1 | 2/2016 | Chou et al. |
| 2016/0036811 A1* | 2/2016 | Shim .................. H04W 12/06 726/7 |
| 2016/0077091 A1* | 3/2016 | Tyrrell .............. G01N 33/48792 436/501 |
| 2016/0245797 A1 | 8/2016 | Ahmad et al. |
| 2016/0266091 A1 | 9/2016 | Levine et al. |
| 2017/0021356 A1 | 1/2017 | Dority et al. |
| 2017/0038401 A1 | 2/2017 | Holmes et al. |
| 2017/0045504 A1 | 2/2017 | Bloom |
| 2017/0196504 A1* | 7/2017 | Kanukurthy .......... A61B 5/1172 |
| 2019/0178869 A1* | 6/2019 | Morley .................. G01N 33/98 |

FOREIGN PATENT DOCUMENTS

| | | |
|---|---|---|
| CN | 1299466 | 6/2001 |
| CN | 1302229 | 7/2001 |
| CN | 1166950 | 9/2004 |
| CN | 1188217 | 2/2005 |
| CN | 102027369 | 4/2011 |
| EP | 261667 A2 | 3/1988 |
| EP | 291153 A1 | 11/1988 |
| EP | 261667 A3 | 5/1989 |
| EP | 291153 B1 | 6/1992 |
| EP | 261667 B1 | 2/1993 |
| EP | 0961110 | 12/1999 |
| EP | 1949310 A2 | 7/2008 |
| EP | 2290100 | 3/2011 |
| EP | 1949310 A4 | 11/2011 |
| EP | 2439515 | 4/2012 |

(56) References Cited

FOREIGN PATENT DOCUMENTS

| | | |
|---|---|---|
| EP | 2554987 | 2/2013 |
| EP | 3026433 | 6/2016 |
| EP | 1949310 B1 | 2/2019 |
| WO | 1991020009 | 12/1991 |
| WO | 1999044743 | 9/1999 |
| WO | 1999045385 | 9/1999 |
| WO | 2003062920 | 7/2003 |
| WO | 2005114145 | 12/2005 |
| WO | 2005100539 | 1/2006 |
| WO | 2007112332 | 10/2007 |
| WO | 2009117652 | 9/2009 |
| WO | 2009117664 | 9/2009 |
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2014055559 | 4/2014 |
| WO | 2014089468 | 6/2014 |
| WO | 2014183049 | 11/2014 |
| WO | 2014205576 | 12/2014 |
| WO | 2017048871 | 3/2017 |

OTHER PUBLICATIONS

International Report on Patentability for PCT/US2018/037168 established by IPEA/US dated Aug. 19, 2019.

\* cited by examiner

A

B

A

B

DEVICES AND METHODS FOR AUTHENTICATING A MEDICAL TEST AND USE OF THE SAME

CROSS-REFERENCE

This application is a National Stage entry (§ 371) application of International Application No. PCT/US2018/055731, filed on Oct. 12, 2018, which claims the benefit of U.S. Provisional Patent Application No. 62/572,121, filed Oct. 13, 2017, the contents of which are relied upon and incorporated herein by reference in their entirety.

The entire disclosure of any publication or patent document mentioned herein is entirely incorporated by reference.

FIELD

The present invention is related to devices and methods for authenticating medical tests, such as a saliva test.

BACKGROUND

Medical tests (such as a saliva test) are widely used for medical, diagnostic, preventive, and screening purposes. In saliva tests, the subject being tested provides a saliva sample either through a "passive drooling" process or through a "oral swab" process conducted by the user or a medical professional.

In a saliva test, sometimes it is important to authenticate the test because it is possible that someone other than the intended subject is actually tested, either inadvertently or deliberately. An "intended subject" is to a person that is scheduled/required to be tested by a testing professional, agency or entity in a specific saliva-testing session. In some instances, for example, an imposter can replace the intended subject and provide a saliva sample of his/her own. In other circumstance, especially in remote saliva tests, the intended subject provides a saliva sample not from himself/herself, but from someone else. Therefore, at least two problems arise: (1) authenticating that the subject being tested is actually the intended subject; and (2) authenticating that the sample being collected is actually a sample from the subject being tested, not from someone else.

The present invention addresses the authentication issues and provides solutions to these problems.

SUMMARY OF THE INVENTION

In accordance with the present invention, one aspect of the invention provides a device for authenticating a saliva sample from an intended subject being tested, comprising: (a) a test plate, the test plate comprises a sample receiving area on its surface that receives a saliva sample from a subject being tested; and (b) a camera, wherein, during a sample deposition process in which a saliva sample is collected and deposited onto the sample receiving area of the test plate, the camera is configured to capture an image that contains at least the following (i) a plate ID that is configured to identify the test plate, (ii) a biometric identifier that identifies the subject being tested, and (iii) a saliva sample that is from the subject being tested and that is deposited onto the test plate, wherein the captured image is used to authenticate that the deposited saliva sample is from an intended subject.

Another aspect of the present invention provides a device for authenticating a saliva sample from an intended subject being tested, comprising (a) a test plate, the test plate comprises a sample receiving area on its surface that receives a saliva sample from a subject being tested; and (b) a camera, wherein, during a sample deposition process in which a saliva sample is collected and deposited onto the sample receiving area of the test plate, the camera is configured to capture a video such as at least one frame of the video contains at least the following: (i) a plate ID that is configured to identify the test plate, (ii) a biometric identifier that identifies the subject being tested, and (iii) a saliva sample that is from the subject being tested and that is deposited onto the test plate, wherein the captured video is used to authenticate that the deposited saliva sample is from an intended subject.

Another aspect of the present invention provides a device for authenticating a saliva sample from a subject being tested, comprising: (a) a test plate, wherein the test plate has (i) a sample receiving area on its surface that receives a saliva sample from a subject being tested, wherein the sample is collected by a swab from the subject's mouth, and (ii) a plate ID that is a unique identifier of the plate; and (b) a camera, wherein, during a sample deposition process in which the saliva sample on the swab is deposited onto the sample receiving area of the test plate, the camera is configured to capture (i') an image that contains the face of the subject being tested when the saliva sample is being collected, and the plate ID, and (ii') a video of a part or an entirety of the saliva sample deposition, wherein the video is used to authenticate that the saliva sample is deposited on the test plate; and wherein the image is used to authenticate that the subject being tested is an intended subject.

Another aspect of the present invention provides a method of authenticating a saliva test, comprising: (a) providing a camera; (b) providing a test plate that has a sample receiving area on its surface; (c) collecting a saliva sample from interior of a subject's mouth using a swab; (d) depositing the saliva sample onto the sample receiving area by touching the test plate with the swab; (e) during the steps of (c)-(d), using the camera to capture at least an image or a video, wherein the image or the video contains: (i) a plate ID that is configured to identify the test plate, (ii) a biometric identifier that identifies the subject being tested, and (iii) a saliva sample that is from the subject being tested and that is deposited onto the test plate; and (f) using the captured image or video to authenticate that the saliva sample deposited onto the test plate is from an intended subject.

Another aspect of the present invention provides a method of authenticating a saliva test, comprising: (a) providing a camera; (b) providing a test plate that has a sample receiving area on its surface; (c) collecting a saliva sample from a subject being tested by passive drooling; (d) depositing the saliva sample onto the sample receiving area of the test plate; (e) during the steps of (c)-(d), using the camera to capture at least an image or a video, wherein the image or the video contains: (i) a plate ID that is configured to identify the test plate,
(ii) one biometric identifier that identifies the subject being tested, and (iii) the saliva sample that is from the subject being tested and that is deposited into the test plate; and (f) using the captured image or video to authenticate that the saliva sample deposited onto the test plate is from an intended subject.

Another aspect of the present invention provides a method of authenticating a saliva test, comprising: (a) providing a test plate that has a sample receiving area on its surface and a plate ID that uniquely identifies the plate; (b) providing a camera; (c) collecting a saliva sample from the interior of a subject's mouth using a swab; (d) depositing the saliva sample onto the sample receiving area by touching the test plate with the swab; and (e) during the deposition process (d), using the camera to capture: (i) an image of the saliva sample together with the face of the subject being tested and the plate ID, and (ii) a video of a part or an entirety of the deposition process and (f) using the captured image or video to authenticate that the saliva sample deposited onto the test plate is from an intended subject.

A device for authenticating a saliva sample from a subject being tested, comprising: a test plate, the test plate comprises a sample receiving area on its surface that receives a saliva sample from a subject being tested; and a camera, wherein, during a sample deposition process in which a saliva sample is collected and deposited onto the sample receiving area of the test plate, the camera is configured to capture an image that contains at least the following: a plate ID that is configured to identify the test plate, a biometric identifier that identifies the subject being tested and a saliva sample that is from the subject being tested and that is deposited onto the test plate, wherein the captured image is used to authenticate that the deposited saliva sample is from an intended subject.

A device for authenticating a saliva sample from a subject being tested, comprising: a test plate, the test plate comprises a sample receiving area on its surface that receives a saliva sample from a subject being tested; and a camera, wherein, during a sample deposition process in which a saliva sample is collected and deposited onto the sample receiving area of the test plate, the camera is configured to capture a video such as at least one frame of the video contains at least the following: a plate ID that is configured to identify the test plate, a biometric identifier that identifies the subject being tested, and a saliva sample that is from the subject being tested and that is deposited onto the test plate, wherein the captured video is used to authenticate that the deposited saliva sample is from an intended subject.

A device for authenticating a saliva sample from a subject being tested, comprising: a test plate, wherein the test plate has: a sample receiving area on its surface that receives a saliva sample from a subject being tested, wherein the sample is collected by a swab from the subject's mouth, and a plate ID that is a unique identifier of the plate; and a camera, wherein, during a sample deposition process in which the saliva sample on the swab is deposited onto the sample receiving area of the test plate, the camera is configured to capture i. an image that contains the face of the subject being tested when the saliva sample is being collected, and the plate ID, and ii. a video of a part or an entirety of the saliva sample deposition, wherein the video is used to authenticate that the saliva sample is deposited on the test plate; and wherein the image is used to authenticate that the subject being tested is an intended subject.

A method of authenticating a saliva test, comprising: providing a camera; providing a test plate that has a sample receiving area on its surface; collecting a saliva sample from interior of an intended subject's mouth using a swab; depositing the saliva sample onto the sample receiving area by touching the test plate with the swab; during the steps of (c)-(d), using the camera to capture at least an image or a video, wherein the image or the video contains:
a plate ID that is configured to identify the test plate, a biometric identifier that identifies the subject being tested, and a saliva sample that is from the subject and that is deposited onto the test plate; and using the captured image or video to authenticate that the saliva sample deposited onto the test plate is from an intended subject.

A method of authenticating a saliva test, comprising: (a) providing a camera; (b) providing a test plate that has a sample receiving area on its surface; (c) collecting a saliva sample from a subject being tested by passive drooling; (d) depositing the saliva sample onto the sample receiving area of the test plate; (e) during the steps of (c)-(d), using the camera to capture at least an image or a video, wherein the image or the video contains: i. a plate ID that is configured to identify the test plate, ii. one biometric identifier that identifies the subject being tested, and iii. the saliva sample that is from the subject being tested and that is deposited into the test plate; and (f) using the captured image or video to authenticate that the saliva sample deposited onto the test plate is from an intended subject.

A method of authenticating a saliva test, comprising: (a) providing a test plate that has a sample receiving area on its surface and a plate ID that uniquely identifies the plate; (b) providing a camera; (c) collecting a saliva sample from the interior of a subject's mouth using a swab; (d) depositing the saliva sample onto the sample receiving area by touching the test plate with the swab; (e) during the deposition process (d), using the camera to capture: i. an image of the saliva sample together with the face of the subject being tested and the plate ID, and ii. a video of a part or an entirety of the deposition process; and (f) using the captured image or video to authenticate that the saliva sample deposited onto the test plate is from an intended subject.

The device or method of any embodiment of the present disclosure, wherein step (e) is performed to capture the plate ID and the biometric identifier about the same time.

The device or method of any embodiment of the present disclosure, wherein the test card is transparent and is positioned in the front of the camera, so that the camera images, at the same time, (i) the card and (ii), through the card, the saliva taking process.

The device or method of any embodiment of the present disclosure comprises a rejection threshold for the sample-to-test time is 2 sec, 5 sec, 10 sec, 20 sec, 20 sec, 30 sec, 60 sec, 80 sec, 100 sec, or a range of any two values, wherein any results with a sample to test time is larger than the threshold is rejected.

The device or method of any embodiment of the present disclosure, wherein the test card is a QMAX card, the camera used in authentication image the boundary of a saliva sample in the QMAX card in a closed configuration, and the camera used in assaying the saliva sample images the boundary of a saliva sample to be tested and compared it with the boundary during the saliva sample taking. If the two images match, the test results will be authenticated, otherwise, the test results will be rejected.

The device or method of any embodiment of the present disclosure, wherein the saliva sample comprises an organic material that is swabbed from a subject mouth.

The device or method of any embodiment of the present disclosure, wherein the biometric identifier is part or entirety of the face of the intended subject being tested.

The device or method of any embodiment of the present disclosure, wherein the biometric identifier is part or entirety of the iris of the subject being tested.

The device or method of any embodiment of the present disclosure, wherein the biometric identifier is part or entirety of the lip pattern of the subject being tested.

The device or method of any embodiment of the present disclosure comprising the image, wherein the image contains the plate ID and the lip pattern of the subject being tested.

The device or method of any embodiment of the present disclosure, wherein the biometric identifier is one of the identifiers: face, iris, retina, lip pattern, ear geometry, skin tone, fingerprint, palmprint, hand geometry, vein pattern, sweat pore pattern, fingernail beds pattern or any combinations of thereof.

The device or method of any embodiment of the present disclosure, wherein the at least two biometric identifiers are used to authenticate that the subject being tested is the intended subject.

The device or method of any embodiment of the present disclosure, wherein the at least three biometric identifiers are used to determine that the subject being tested is the intended subject.

The device or method of any embodiment of the present disclosure, wherein sample deposition process comprises collecting the saliva sample from the interior of the subject's mouth with a swab.

The device or method of any embodiment of the present disclosure, wherein the saliva sample is collected by saturating the swab under the tongue of the subject being tested.

The device or method of any embodiment of the present disclosure, wherein sample deposition process comprises touching the sample receiving area with the swab after collecting the saliva sample.

The device or method of any embodiment of the present disclosure, wherein sample deposition process comprises collecting the saliva sample with passive drooling.

The device or method of any embodiment of the present disclosure, wherein at least one image is recorded before the saliva sample touches the sample receiving area.

The device or method of any embodiment of the present disclosure, wherein at least image is recorded after the saliva sample touches the sample receiving area.

The device or method of any embodiment of the present disclosure, wherein the images are recorded both before and after the saliva sample touches the sample receiving area.

The device or method of any embodiment of the present disclosure, further comprising hardware and software which are configured to process and analyze the images/videos.

The device or method of any embodiment of the present disclosure, wherein the hardware is a mobile phone and has local and long-distance communication capacities.

The device or method of any embodiment of the present disclosure, wherein the positions of the test plate and the camera are configured to have the camera imaging the facial features of the subject being tested and deposition of the saliva sample on the test plate in the same image frame.

The device or method of any embodiment of the present disclosure, wherein: the test plate is partial or completely transparent, the camera records the saliva deposition process from a side opposite to the sample receiving surface of the test plate, and the camera images the biometric identifier of the subject being tested and deposition of the saliva sample on the test plate in the same image frame.

The device or method of any embodiment of the present disclosure, wherein the device further comprises an optical fiber that is configured to image the face of the subject being tested or the test plate by camera.

The device or method of any embodiment of the present disclosure, wherein the camera is a part of mobile phone.

The device or method of any embodiment of the present disclosure, wherein the camera is a part of mobile phone, wherein the mobile phone has a second camera for testing the test plate.

The device or method of any embodiment of the present disclosure, wherein the test plate comprises a plate ID that is a is a sequence of digital and/or alphabetical characters, a 1-D barcode, a 2-D barcode, a QR code, a watermark, a waveform, or other machine-readable non-letter type code.

The device or method of any embodiment of the present disclosure, wherein the camera is configured to capture an image or video that includes the plate identification.

The device or method of any embodiment of the present disclosure, wherein the camera is configured to capture images or videos of the saliva sample, the biometric identifier, the test plates, and the plate identification.

The device or method of any embodiment of the present disclosure, wherein: the test plate is sealed in a package before the saliva test; and the package comprises a package ID.

The device or method of any embodiment of the present disclosure, wherein the package ID is paired with the plate ID and the pairing is unknown to the subject being tested.

The device or method of any embodiment of the present disclosure, wherein the device is used for health monitoring, mobile monitoring, crime monitoring, for insurance, for health, and/or for medication.

The device or method of any embodiment of the present disclosure, wherein the test plate is further configured to prevent sample switching after the deposition.

The device or method of any embodiment of the present disclosure, wherein the prevention of sample switching comprises using of a CROF (Compressed Open Flow) test plate.

The device or method of any embodiment of the present disclosure, wherein the camera is further configured to capture the time points of:
collecting the saliva sample from the interior of the subject's mouth using a swab; and depositing the saliva sample by touching the test plate with the swab.

The device or method of any embodiment of the present disclosure, further comprising a processor, wherein the processor is configured to: analyze the image of the biometric identifier captured by the camera; compare the biometric identifier with stored biometric identifier information of the subject; and determine whether the saliva sample provided in the saliva test is from the intended subject.

The device or method of any embodiment of the present disclosure, wherein the test plate is part of a QMAX device (e.g. Q-card).

The device or method of any embodiment of the present disclosure, wherein the device further comprises a cover plate that is configured to cover the test plate.

The device or method of any embodiment of the present disclosure, further comprising: analyzing the one or more images or video that include the biometric identifier; comparing the biometric identifier to stored biometric information from the intended subject; and determining whether the saliva provided in the saliva test is from the intended subject.

The device or method of any embodiment of the present disclosure, further comprising: analyzing the video of the sample depositing process; and determining whether the saliva sample is produced by the subject being tested.

The device or method of any embodiment of the present disclosure, wherein analyzing the image comprises evaluation of the geometry and/or shape of the saliva sample on the pricked finger.

The device or method of any embodiment of the present disclosure, further comprising: using the camera to capture a time point for depositing the saliva sample on the test plate.

The device or method of any embodiment of the present disclosure, wherein the biometric information is stored in a local device, a cloud, or a combination thereof.

The device or method of any embodiment of the present disclosure, wherein the comparison of the biometric identifier and the biometric information is conducted with a local device, a remote device, or a combination thereof.

BRIEF DESCRIPTION OF THE DRAWINGS

A skilled artisan will understand that the drawings, described below, are for illustration purposes only, and are not necessarily in scale. The lines that connect the data points in the drawing are for guiding a viewing of the data only and have no other means. The drawings are not intended to limit the scope of the present teachings in any way.

DETAILED DESCRIPTION OF EXEMPLARY EMBODIMENTS

Figure 1:
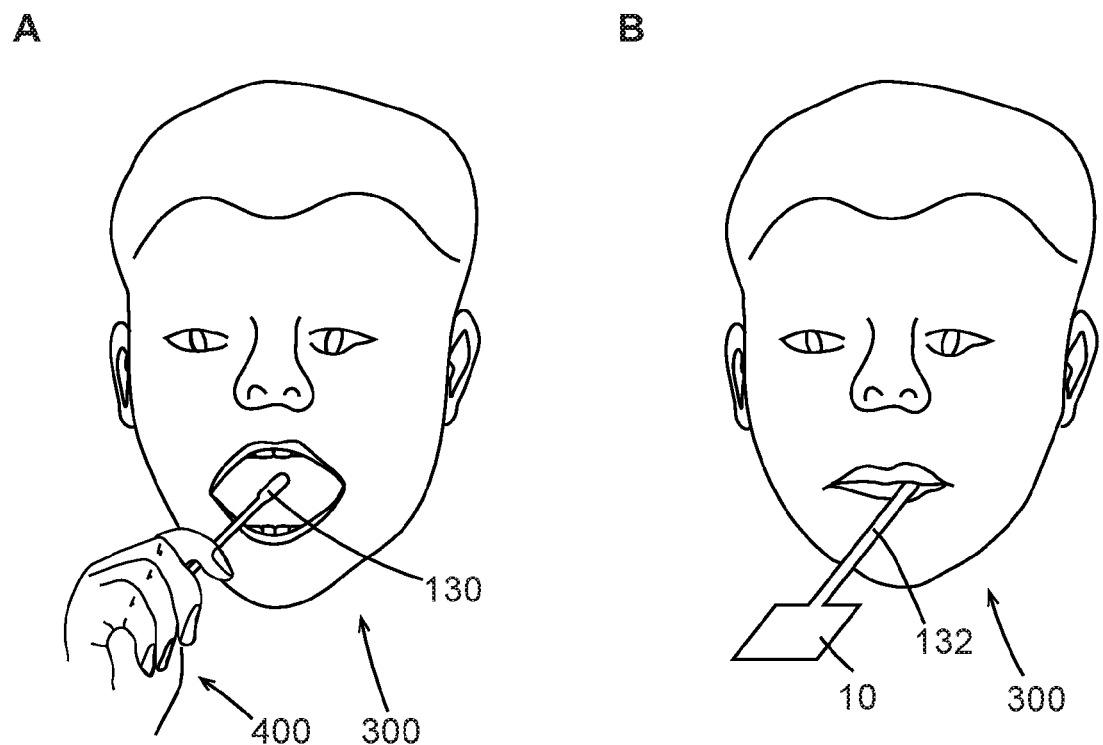
FIG. 1 illustrates the two processes to collect saliva sample; panel (A) shows the oral swab process in which the subject being tested uses a swab to collect saliva; panel (B) shows the passive drooling process in which the subject being bested uses a saliva collector and drool the saliva sample into the collector.

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

One aspect of the present invention for the saliva sample authentication is to use a saliva sample collected with an oral swabbing process, and use a camera to record the collection and deposition of the sample on a test plate. The recorded images contain: (i) the saliva sample collected with the swab together with at least one biometric identifier associated with the subject being tested, and (ii) a video of a part or an entirety of the saliva sample deposition process.

One aspect of the present invention for the saliva sample authentication is to use a saliva sample collected with an passive drooling process, and use a camera to record the collection and deposition of the sample on a test plate, The recorded images contain: (i) the saliva sample collected with the passive drooling collector together with at least one biometric identifier associated with the subject being tested, and (ii) a video of a part or an entirety of the saliva sample deposition process.

Biometric identifier includes characteristics that are unique for each subject and guarantees the authentication of the sample source comes from the subject. The biometric identifier includes physical or biological characteristics which includes, but not limited to face, iris, retina pattern, lip pattern, ear geometry, skin tone, fingerprint, palmprint, hand geometry, vein pattern, sweat pore pattern, fingernail beds pattern, and the like. In certain preferred embodiments, the biometric identifier is a face, or features of a face.

Suitable biological characteristics typically are not under the control of the person, and are therefore difficult for anyone besides the intended person to present, because, in part, they are difficult to replicate. The verifier typically can observe the biological characteristic, and compare the biological characteristic to records that associate the biological characteristic with the particular subject. In cases where the biometric identifier information does not match with the recorded database, the sample will not be proceeded to be tested.

Personal authentication includes biometric identifier information about the subject such as the subject's fingerprint, voiceprint, retina pattern, iris, face, signature and the like. The present system may be configured with a portable personal build-in communication means and reading means for reading at least one of the biometric identifier information of the subject. The biometric identifier information can be registered in advance, for example, recorded and stored in the portable personal authentication apparatus. The biometric identifier information is unique for each subject and thus guarantees the authentication of the sample source comes from the intended subject.

The personal authentication system can be managed by connecting to a mobile device. By authenticating the person concerned in the case of sample donation, the system is designed to eliminate unintentional mistakes or evil intents and increases the reliability of the diagnosis.

In certain embodiments, a photo of a face may be used for authentication; alternatively, a human lip pattern can also serve for authentication. An iris, which represents a round-shape membrane in front of the lens surrounding the pupil, is unique for each subject and can reliably serve as another authentication means.

Fingerprint has long been used in criminal investigation. Because it is generally known not to change over the lifetime, it is used to identify an individual. In certain embodiments, fingerprint can be used as a means of authentication in this invention. Methods for obtaining and comparing fingerprints are well known in the art.

Other personal biometric information can be taken and stored in computer system. The present personal authentication system is configured to contain data memory capability.

In general, the devices and methods of the present invention can be used in health monitoring, disease prevention, mobile monitoring, and crime monitoring. In addition, the devices and methods the present invention can be used for insurance, for health improvement, and/or for medication purposes.

In some saliva tests, the subject that is being tested provides a saliva sample from the mouth. Either directly or indirectly, the saliva is applied to a plate as a saliva sample that would be tested.

The present invention relates to devices and methods that authenticate a saliva sample. In particular, with the devices and methods of the present invention, it can be determined: (1) whether the subject being tested is the intended subject; and (2) whether the saliva sample deposited on the test plate is from the subject being tested, and not from someone else.

The term "intended subject" used herein refers to a person that is scheduled/required to be tested in a specific saliva-testing session by a testing professional, agency or entity. The term "subject being tested" (or simply "subject") used herein refers to a person that is participating in the saliva-testing session; however, it is possible that the subject being tested is not the intended subject; and/or the subject being tested is not providing saliva sample from himself/herself.

Multiple processes can be used to collect a saliva sample. FIG. 1 illustrates two specific exemplary processes to collect saliva sample. As shown in panel (A), in an oral swab process, the subject being tested uses a swab 130 to collect saliva. In certain embodiments, the oral swab process comprises: (i) providing a swab, which comprises a non-toxic, hygienic and absorbent material; (ii) inserting a swab into the mouth of the subject being tested and allowing the swab to contact saliva generated by the subject, optionally the swab can be soaked in saliva for a period of time; and (iii) contacting a test plate (not shown in FIG. 1; referring to FIG. 3) with the swab which has been moistened by saliva, depositing saliva on a sample receiving area of the test plate.

As shown in panel (B), in passive drooling process, the subject being bested uses a collector medium 132 and drool the saliva sample into the test plate 10. In certain embodiments, the passive drooling process comprises: (i) providing a saliva collector, which comprises a collector medium 132 and a test plate 10; and (ii) inserting a collector medium 132 into the mouth of the subject being tested so that the subject can produce saliva that flows through the collector medium 132 onto the test plate 10; thus depositing saliva on a sample receiving area of a test plate.

It should be noted that it is possible that test plate 10 is not directly connected with the collector medium 132. In certain embodiments, the collector medium 132 is connected to a collector body, which can be any container that contains the saliva sample; then the saliva sample in the container is deposited on the test plate 10.

As used herein, a "sample deposition process" is be used to refer to all the steps that are used to collect and deposit the saliva sample, either with the oral swab process or with the passive drooling process.

To authenticate the saliva test, the identity of the subject being tested need to be confirmed as the same for the intended subject. In certain embodiments, the devices and methods of the present invention entails collecting at least one biometric identifier from the subject being tested. Here, the term "biometric identifier" refers to biological traits related to human characteristics and such biological traits can be used to uniquely identify a human. The biometric identifier in the present invention includes but not is limited to: fingerprints, palmprints, hand geometry, vein patterns, sweat pores, fingernail beds, face, iris, retina, DNA, gait, ear, skin tone, lip motion, body odor, and footprint.

In addition to the swab 130 and the saliva collector 15, panels (A) and (B) of FIG. 1 also show the face 300 of the subject being tested. Therefore, the face 300, and the features associated with the face and other body parts on the face, can provide the biometric identifier necessary for the determination of the identity of the subject being tested. In addition, panel (A) also shows the hand 400 of the subject being tested assuming that the sample collection process is self-conducted.

It should be noted that the process can be conducted by another person (e.g. a medical professional), in which case the hand cannot be used to provide the biometric identifiers. Moreover, if the hand, or any other body part of the subject being tested, can be imaged in either the oral swab process or the passive drooling process, the biometric identifiers thereof are used to accurately determine whether the subject being tested is the intended subject.

The images shown in panels (A) and (B) of FIG. 1 provides an example for the biometric identifier that is captured/recorded with the devices and methods of the present invention. In certain embodiments, the devices and methods of the present invention use at least one biometric identifier related to the face 300 to verify that the subject being tested is the intended subject; the biometric identifier related to the face includes but not are limited to: face pattern, iris pattern, retina pattern, ear geometry, skin tone, sweat pore pattern and vein pattern. In some embodiments, the hand is used to provide the biometric identifiers that are used to verify that the subject being tested is the intended subject; the biometric identifier related to the hand include but not limited to: fingerprint, palmprint, hand geometry, vein pattern, sweat pore pattern, skin tone, or fingernail beds pattern.

Figure 2:
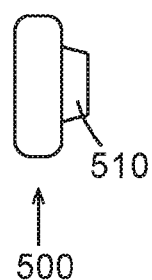
FIG. 2 illustrates exemplary embodiments of the present invention, showing the device and process of authenticating the sample in the oral swab (panels (A)) process and the passive drooling (panel (B)) process when the sample is being collected.
Figure 2:
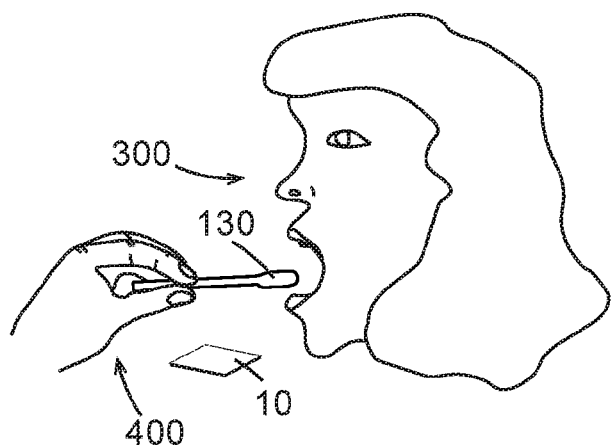
Figure 2:
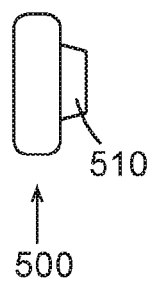
Figure 2:
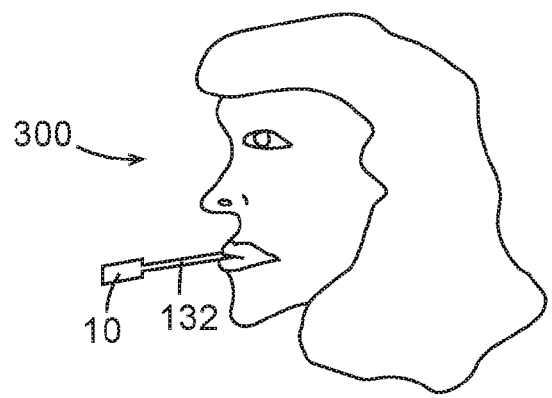

FIG. 2 includes illustrations of exemplary embodiments of the present invention, showing the devices and processes of authenticating the sample in the oral swab (panels (A)) process and the passive drooling (panel (B)) process when the sample is being collected. As shown in FIG. 2, panels (A) and (B), the devices of the present invention comprise a test plate 10 and a camera 500, which comprises a lens 510.

Figure 3:
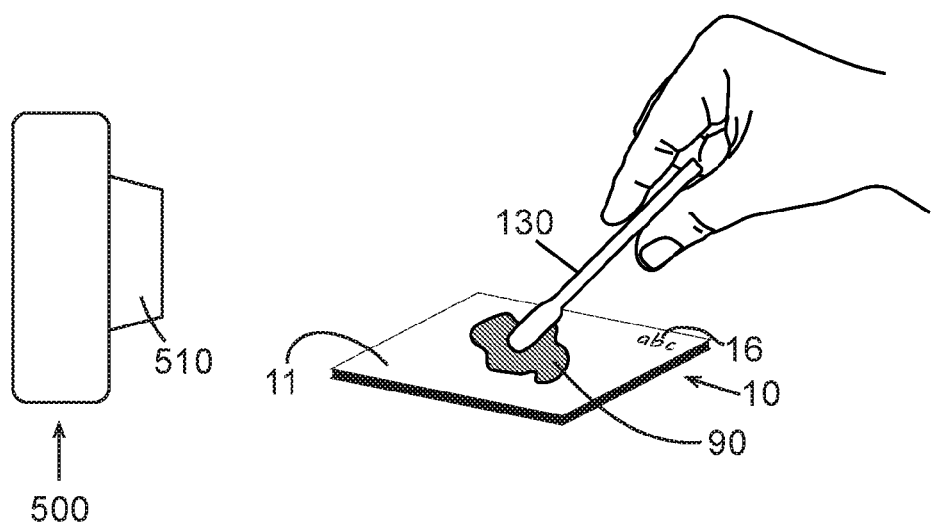
FIG. 3 illustrates exemplary embodiments of the present invention, showing the device and process of authenticating the sample in the oral swab (panels (A)) process and the passive drooling (panel (B)) process after the sample has been collected.
Figure 3:
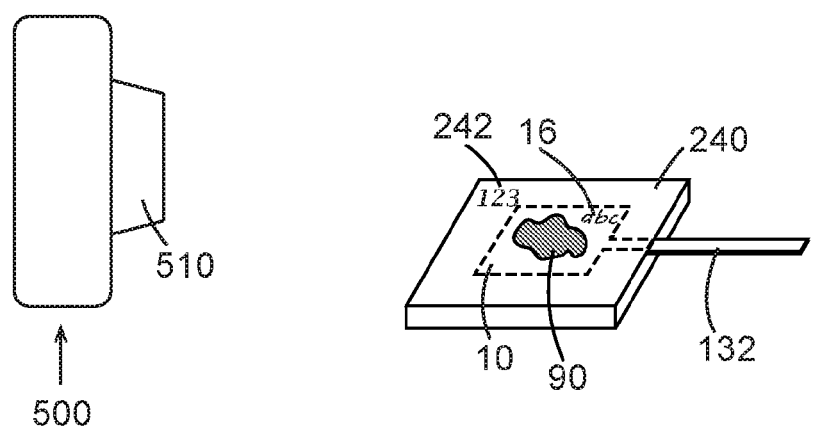

As also shown in FIG. 3, panels (A) and (B), the test plate 10 is configured to receive the saliva sample from a subject that is being tested either by the oral swab process (panel (A) or by the passive drooling process (panel (B)), and the saliva sample is to be deposited on the sample receiving surface 11 by the subject. Herein the term "subject" refers to the individual who is using the test plate 10 for the saliva test, and sometimes the term "subject being tested" is also used. In some embodiments, the subject is a person.

FIG. 3 includes illustrations of exemplary embodiments of the present invention. The device of the present invention comprises a camera 500 and a test plate 10. Panels (A) shows depositing the sample on the test plate 10 after an oral swab has acquired the saliva from the mouth of the subject being tested. As shown in panel (A) of FIG. 3, the test plate 10 comprises a sample receiving surface 11 that has a sample receiving area 110. By contacting the sample receiving surface 11 of the test plate 10 with the swab 130, at least part of the sample on the swab 130 is deposited on the sample receiving surface 11.

Panel (B) of FIG. 3 shows a certain embodiment of the device of the present invention after the sample has been collected with the passive drooling process. The device comprises a camera 500 and a test plate 10. The test plate 10 comprises a sample receiving surface that has a sample receiving area. In certain embodiments, the saliva sample flows directly from the collector medium 132 to the test plate 10. In certain embodiments, the saliva sample is acquired through capillary effects. In certain embodiments, the saliva sample is first collected into a collector body (container) and then deposited on the test plate 10. As shown in panel (B) of FIG. 3, in certain embodiments, the test plate 10 and/or the collector medium 132 is secured and/or covered with an enclosing member 240. As shown in panel (B) of FIG. 3, in some embodiments, the enclosing member 240 encloses the test plate 10 to prevent tempering of the sample 90. In certain embodiments, the enclosing member 240 enclose part of the entirety of the collector medium 132; in certain embodiments, the collector medium 132 is removed so that the enclosing member 240 only encloses the test plate 10; in certain embodiments, only the entity/agency/professional administering the saliva test can open the enclosing member 240 without damaging the test plate 10; in other words, in certain embodiments the enclosing member 240 is locked.

Figure 4:
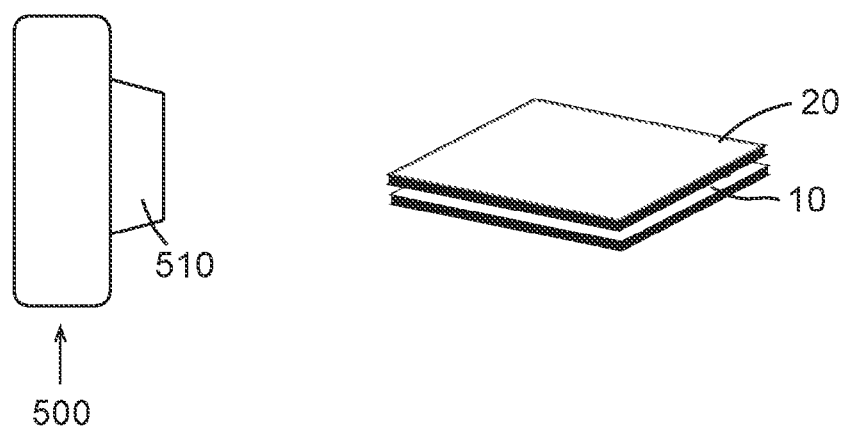
FIG. 4 illustrates an exemplary embodiment of the present invention, showing a device comprising a test plate, a cover plate and a camera.

FIG. 4 illustrates an exemplary embodiment of the present invention, showing a device comprising a test plate 10, a cover plate 20 and a camera 500, wherein the test plate 10 and the cover plate 20 are aligned against each other in a closed configuration.

As shown in FIGS. 2-4, in some embodiments, the sample receiving surface 11 of the first plate 10 comprises a sample receiving area 110. In certain embodiments, the sample receiving area 110 occupy a part or the entirety of the sample receiving surface 11.

In certain embodiments, the sample receiving area 110 is clearly marked so that the subject easily deposits the saliva sample into the sample receiving area 110. In certain embodiments, the test plate 10 comprises additional structures that are located in the sample receiving area 110, wherein such additional structures improve and/or facilitate the saliva test. For example, the additional structures are spacers or grids.

To authenticate a saliva test, a camera 500 is configured to capture videos and/or images of the subject, the face 300, the hand 400, the swab 130, the collector medium 132 and/or the test plate 10, as well as any features associated with these structures, such as but not limited to biometric identifiers (e.g. face features of the face 300) associated with the subject being bested and the sample being collected. In certain embodiments, the video and/or image(s) are used to: (a) determine that the saliva sample 90 deposited on the test plate is actually from the subject being tested; and (b) determine that the subject being tested is the intended subject.

In certain embodiments, the camera 500 and the test plate 10 are physically integrated together, e.g. in a single housing structure. In certain embodiments, the camera 500 and the test plate 10 are partially or entirely separated apart but are considered parts of one device.

In certain embodiments, the camera 500 is configured to capture one or more images and/or one or more videos of the saliva sample 90 before and/or after it is deposited on the test plate 10. Such image(s) and video(s) include at least one biometric identifier of the subject being tested; the biometric identifier is associated with the face and/or the hand of the subject being tested. Part of the descriptions below uses face features as an example; however, in some embodiments of the present invention, other biometric identifiers are captured, extracted and used for authentication purposes. Here, the phrase "face features" refer to features that are sufficient for facial recognition of a person; for example, face features include but not are limited to relative position, size, and/or shape of the eyes, nose, ears, eyebrows, mouth, forehead, temple, chin, jaw, lip pattern, nosebridge, and cheekbones that can be used for facial recognition, especially facial recognition with computer devices. The descriptions related to face features also apply to other biometric identifiers, as long as no clear conflict arises.

In certain embodiments, the camera 500 is configured to capture an image of the face of the subject being tested during a process of providing the saliva sample for testing, such as but not limited to during the oral swab process and/or the passive drooling process. In certain embodiments, the camera 500 is configured to capture one or more images of the face of the subject being tested, including at least part of the face and/or face features sufficient for facial recognition, during the saliva sample deposition process. The image(s) of the face are used to authenticate the saliva test, for example, through a comparison of the face features to stored face feature information of the intended subject. In such a manner, it can be determined whether the subject using the test plate 10 is actually the intended subject. In some embodiments, the presence of the hand, the swab and/or the collector medium make it more difficult for the camera 500 to capture an image of the entire face. Nevertheless, with known technology for partial facial recognition (e.g. the devices, methods and technology disclosed in U.S. Pat. Nos. 7,817,826 and 8,363,951, which are incorporated by reference), as long as the captured image includes part of the face that can be processed to produce facial information for identification, the image would be acceptable.

As shown in FIG. 3, in the same image, the camera 500 is configured to capture: (a) the saliva sample being collected, together with (b) the face of the subject being tested. In certain embodiments, the camera 500 captures one image and at least two types of information are extracted from the image. The information includes: (1) the face feature information that is used to verify the identity of the subject being tested; and (2) information related to the saliva sample and the test plate 10 (e.g. plate number 16 on the test plate 10; see e.g. FIG. 3), which is used to identify the sample after it has been deposited. The information related to the saliva sample is used to determine whether the saliva sample is from the person being tested.

In certain embodiments, the camera 500 is also be configured to record a video of a part or the entirety of the process of providing the saliva sample 90 for testing. Such a recording ensures that the saliva sample is actually produced by the subject being tested, not from other sources such as but not limited to saliva prepared beforehand by the subject. In certain embodiments, the camera 500 captures the image of the face of the subject being tested while recording the video of the oral swab process and/or the passive drooling process. In certain embodiments, recording a video of the saliva sample deposition process for testing would generate a comprehensive and continuous record of the process, allowing the agency/entity/professional that is administering/supervising the testing to be able to monitor, control and authenticate the saliva test in full. From the video, it would be clear whether the subject conducted and completed the saliva sample deposition process for testing. In certain embodiments, it would be sufficient and/or necessary to record only part of the process of the saliva sample deposition process. For example, in certain embodiments, only the process of collecting the saliva sample is recorded; in certain embodiments, only the process of depositing the saliva sample on the test plate 10 is recorded; in certain embodiments, only part of the collection process and/or part of the depositing process is recorded. Such an approach would reduce file size for the recorded data and is still sufficient to determine: (1) whether the saliva sample is actually produced the subject being tested, and (2) whether the saliva is deposited on the sample receiving surface 11 of the test plate 10.

In certain embodiments, it is impractical, difficult, or unnecessary to use the camera 500 to record a lengthy video of the saliva sample depositing process. Therefore, in certain embodiments, the camera 500 is configured to capture one or more images during the process of providing the saliva for testing. For instance, in some embodiments, the camera 500 is configured to capture an image of the saliva sample and the face of the subject being tested before the saliva is deposited. Such an image is used to verify that the saliva sample is actually collected from the mouth of the subject being tested. In some embodiments, the camera 500 is configured to capture at least two images of the saliva sample, one image before the depositing and one image after the depositing. An analysis of the images and a comparison of them reveals: (1) whether the saliva sample is actually produced from the mouth of the subject being tested, and (2) whether the saliva in the first image is actually deposited on the sample receiving surface 11 of the test plate 10.

In certain embodiments, the camera 500 includes a timing component, which records the particular time points during the saliva sample deposition process. For example, the time point of swabbing the mouth is recorded to start at US Eastern Time 2016-12-01 9:30:25 AM; the time point of depositing the saliva is recorded as US ET 2016-10-01 9:34:25 AM. The recording of the time point(s) is conducted by the timing component of the camera 500, or conducted by a timing component physically separated from the camera 500 but still be considered part of a single device. The recorded time points are used to add another layer of authentication for the saliva test. For example, the recorded time can be compared with other records to verify whether the saliva sample deposition process for testing is conducted at the prescribed time by the agency/entity/professional administering the test. In addition, the time period between the recorded time points provides further information/suspicion about the authenticity of the saliva test. For instance, if there is a ten-minute gap between the time point of starting the oral swab and the time point of depositing the saliva, then it becomes suspicious as to whether the saliva collected by oral swab is actually the saliva sample deposited on the test plate 10. A follow-up investigation, which involves a viewing/analysis of a video of the saliva sample deposition process, is conducted.

In certain embodiments, the devices of the present invention further comprise a processor, which is configured to process the images and/or video captured by the camera 500. The processor is a component of the camera 500 or is integrated with the camera 500 physically into a single structure. For example, the processor and the camera 500 are both parts of a computing device, such as but not limited to a mobile phone, a tablet computer or a laptop computer. Alternatively, the processor, the camera 500, the timing component are all part of a computing device, such as but not limited to a mobile phone, a tablet computer or a laptop computer. In addition, the processor, the camera 500, the timing component, and the test plate 10 are all parts of device. In certain embodiments, the parts are integrated together and in certain embodiments, the parts are separated apart.

In certain embodiments, the processor is configured to process and analyze the images and videos captured by the camera 500. For example, in certain embodiments, the processor is configured to: (1) analyze the image of the face of the subject being tested after the image has been captured by the camera 500, (2) compare the face features with stored face feature information of the intended subject; and/or (3) determine whether the saliva provided in the saliva test is from the intended subject. In certain embodiments, the processor is configured to: analyze the image(s) and/or videos of the saliva sample deposition process, and determine whether the saliva sample truly produced by the subject being tested.

It should also be noted that the positioning of the camera 500 and the test plate 10, as well as other components of the device of the present invention, can vary according to the specific designs of verification process and the specific protocol to capture which type of image(s) and/or video(s). In general, when the test plate 10 is positioned horizontally, the plane in which the test plate 10 is positioned divides the relative space into a top space, which faces the sample receiving surface 11, and a bottom space, which faces a non-sample receiving surface of the test plate 10 opposite to the sample receiving surface 11.

As shown in FIG. 2, the camera 500 is positioned in the top space; the lens 510 of the camera 500 is pointed to the face of the subject being tested and the saliva sample, allowing the camera 500 to capture the image(s) and/or video(s) of the saliva sample deposition process. In some embodiments, the lens 510 is perpendicular to the sample receiving surface 11. In certain embodiments, the camera 500 is positioned in the bottom space; and the lens 510 of the camera 500 faces a non-sample receiving surface of the test plate. In certain embodiments, the test plate 10 is partly or entirely transparent, and the camera 500 is configured to capture the images through the test plate 10.

After saliva sample is deposited on the test plate 10, further processing, testing and/or analysis are conducted. For example, as shown in FIG. 4, the devices of the present invention further comprise a cover plate 20, which is used to cover the test plate 10 so that the sample is squeezed into a thin layer for further analysis. In certain embodiments, the devices comprise spacers fixed on one or both of the test plate 10 and the cover plate 20, or the spacers are mixed with a sample.

In certain embodiments, after the plates are compressed into a face-to-face configuration, the spacers regulate the spacing between the plates. If the sample has been deposited, all or part of the sample is compressed into a thin layer that has a uniform thickness with a small variation. The sample then is analyzed for certain properties, such as but not limited to: adrenal conditions (e.g. for Cushing's disease/syndrome and Addison's disease), altered female hormone states (e.g. for polycystic ovary syndrome, menopause, anovulation, and hormonal alterations in cycling women), altered male hormone states (e.g. for hypogonadism/andropause and hyper estrogenic states), metabolic disturbances (e.g. glucose levels for insulin resistance, diabetes, and metabolic syndrome), benign and metastatic neoplasms (e.g. for breast cancer, pancreatic cancer, and oral cancer), infectious conditions (e.g. for HIV, viral hepatitis, amoebiasis, and Helicobacter pylori infection), and allergic conditions (e.g. for food allergy).

In certain embodiments, the saliva sample comprises an organic material that is swabbed from a subject mouth (e.g. the organic material for DNA testing)

In certain embodiments, the test plate 10 is part of a QMAX (Q: quantification; M: magnifying; A: adding reagents; X: acceleration; also known as compressed regulated open flow (CROF)) device, such as but not limited to the QMAX (or CROF) device described in U.S. Provisional Patent Application No. 62/202,989, which was filed on Aug. 10, 2015, U.S. Provisional Patent Application No. 62/218,455, which was filed on Sep. 14, 2015, U.S. Provisional Patent Application No. 62/293,188, which was filed on Feb. 9, 2016, U.S. Provisional Patent Application No. 62/305,123, which was filed on Mar. 8, 2016, U.S. Provisional Patent Application No. 62/369,181, which was filed on Jul. 31, 2016, U.S. Provisional Patent Application No. 62/394,753, which was filed on Sep. 15, 2016, PCT Application (designating U.S.) No. PCT/US2016/045437, which was filed on Aug. 10, 2016, PCT Application (designating U.S.) No. PCT/US2016/051775, which was filed on Sep. 14, 2016, PCT Application (designating U.S.) No. PCT/US2016/051794, which was filed on Sep. 15, 2016, and PCT Application (designating U.S.) No. PCT/US2016/054025, which was filed on Sep. 27, 2016, the entire disclosures of which are hereby incorporated by reference for all purposes. In certain embodiments, the devices of the present invention comprise both the test plate 10 and the cover plate 20. In certain embodiments, the combination of the test plate 10 and the cover plate 20 is called a QMAX card.

As shown in FIG. 3, the test plate 10 comprises a plate identification (ID) 16. In certain embodiments, with the plate identification (ID) 16, the test plate is further configured to prevent sample switching after the deposition as well as verification of the saliva sample deposition process. The plate ID 16 can include any combination of numerical, alphabetical, symbolic or other characters and signs, as long as the plate ID 16 can be used to identify the test plate 10 uniquely. In certain embodiments, the plate ID 16 is positioned on the sample receiving surface 11 of the test plate 10, as shown in FIG. 3. In certain embodiments, the plate ID 16 is also positioned on other parts of the plate, e.g. on the non-sample receiving surface of the test plate 10. In certain embodiments, the camera 500 is configured to capture an image of the plate ID 16 during the process of providing a drop of saliva for testing. For example, when taking the image of the fingerprint of the pricked finger 900 and/or recording a video of the process of providing a drop of saliva for testing, the camera 500 captures one or images of the test plate 10 and such images show the plate ID 16.

In certain embodiments, the plate ID 16 is used to identify the test plate 10, as well as the saliva sample deposited on the test plate 10. In certain embodiments, the plate ID 16 is also combined with the face feature information extracted from the image(s) and/or video(s) taken during the saliva sample deposition process. For example, it would be possible to match the extracted face feature information to stored face feature information of the intended subject, and at the same time use the plate ID and the video(s)/image(s) captured during the saliva sample deposition process for testing to clearly identify the test plate 10 and ensure that the face features match the video(s)/image(s) on record. In some embodiments, the presence of the plate ID 16 allows the agency/entity/professional administering the test to prevent switching the plate after the sample has been deposited. In certain embodiments, to prevent switching, a QMAX card is used.

As indicated, besides face features, in some embodiments of the present invention, other biometric identifiers are used for identification of the subject being tested. For example, in certain embodiments of the present invention, the biometric identifier is the iris of the subject being tested, where iris structures/patterns are used for biometric identification through the analysis of such structures/patterns. The image(s)/video(s) captured by the camera 500 provide iris structures/patterns and the iris structures/patterns are compared to information on file for the intended subject. In certain embodiments, the technologies to verify iris structures/patterns information are known. In certain embodiments, such technologies include but are not limited to the devices, apparatus, and methods disclosed in U.S. Pat. Pub. No. 2015/0062324 and U.S. Pat. Nos. 4,641,349, 5,572,596, 6,714,665, 7,920,724, 7,924,058, 8,374,404, 8,411,910, 8,452,131, 8,705,808, 8,913,119, 9,002,053, and 9,122,926, the disclosures of which are all incorporated by reference in their entireties.

In certain embodiments of the present invention, the biometric identifier is the retina of the subject being tested, where retinal patterns are used for biometric identification through the analysis of such patterns, e.g. by retinal scan. The image(s)/video(s) captured by the camera 500 provide retinal patterns and the retinal patterns are compared to information on file for the intended subject. In certain embodiments, the technologies to verify retinal pattern information are known. In certain embodiments, such technologies include but are not limited to the devices, apparatus, and methods disclosed in U.S. Pat. Pub. Nos. 2004/0233038, 2011/0013246 and 2011/0199582 and U.S. Pat. Nos. 5,359,669, 5,369,415, 5,845,733, 8,072,666, 8,422,750, and 8,514,277, the disclosures of which are all incorporated by reference in their entireties. In some embodiments of the present invention, the camera 500 has infrared photography capacity.

In certain embodiments of the present invention, the biometric identifier is ear geometry of the subject being tested, where the 3-D geometry of the ears of the subject being tested are used for biometric identification through the analysis of such geometry. The image(s)/video(s) captured by the camera 500 provide geometry of the ears, and such information is compared to information on file for the intended subject. In certain embodiments, the technologies to verify ear geometry information are known. Such technologies include but are not limited to the devices, apparatus, and methods disclosed in U.S. Pat. Pub. Nos. 2008/0013794 and 2008/0285813 and U.S. Pat. Nos. 7,065,232 and 7,826,643, the disclosures of which are all incorporated by reference in their entireties.

In certain embodiments of the present invention, the biometric identifier is skin tone of the subject being tested, where the skin tone of the subject is used for precise or approximate biometric identification through the analysis of the skin tone. The image(s)/video(s) captured by the camera 500 provide the skin tone, which is compared to information on file for the intended subject. In certain embodiments, the technologies to detect skin tone information are known. Such technologies include but are not limited to the devices, apparatus, and methods disclosed in U.S. Pat. Pub. Nos. 2009/0263013 and 2010/0322513 and U.S. Pat. Nos. 7,844,076, 8,131,029, 8,406,482, 8,121,430, 8,369,486, 8,861,487 and 8,908,932, the disclosures of which are all incorporated by reference in their entireties. In certain embodiments, if the skin tone information cannot provide conclusive results, additional steps can be taken to further identify the subject being tested. For example, another biometric identifier is used when the skin tone information produces suspicion.

In certain embodiments of the present invention, the biometric identifier is the vein pattern of the face and/or hand, where vein patterns (or vascular patterns) are used for biometric identification through the analysis of the patterns of blood vessels visible from the surface of the skin. The image(s)/video(s) captured by the camera 500 provide vein pattern of the face and/or hand and the vein pattern are compared to information on file for the intended subject. In some embodiments, the technologies to verify vein pattern information are known. In certain embodiments, such technologies include but are not limited to the devices, apparatus, and methods disclosed in U.S. Pat. Pub. Nos. 2014/0196131, 2010/0119122 and 2010/0226545, and U.S. Pat. Nos. 8,803,963, 9,095,285, 9,289,160, 8,509,495, 8,275,174 and 9,317,761, the disclosures of which are all incorporated by reference in their entireties.

In certain embodiments of the present invention, the biometric identifier is sweat pores of the face and/or hand, where positions and patterns of the sweat pores are used for biometric identification of the subject. The image(s)/video(s) captured by the camera 500 include sweat pores of the hand and the sweat pores are compared to information on file for the intended subject. In some embodiments, the technologies to verify sweat pores information are known. Such technologies include but are not limited to the devices, apparatus, and methods disclosed in U.S. Pat. Pub. Nos. 2007/0003114 and 2014/0294262, and U.S. Pat. Nos. 6,228,029, 8,663,108, and 8,744,139, the disclosures of which are all incorporated by reference in their entireties.

In certain embodiments the biometric identifier is palmprints, which are shown in FIG. 1. The image(s)/video(s) captured by the camera 500 include palmprints of the hand and the palmprints are compared to the palmprint information on file for the intended subject. In some embodiments, the technologies to verify palmprint information are known. Such technologies include but are not limited to the devices, apparatus, and methods disclosed in U.S. Pat. Pub. Nos. 2012/0194662 and 2005/0281438, and U.S. Pat. Nos. 8,229,178, 7,466,846, 8,135,181, 8,265,347, and 7,496,214, the disclosures of which are all incorporated by reference in their entireties.

In certain embodiments of the present invention, the biometric identifier is hand geometry, which is a biometric that identifies users by the shape of their hands. In known technologies, hand geometry readers measure a user's hand along many dimensions and compare those measurements to measurements stored in a file. The image(s)/video(s) captured by the camera 500 provide hand geometry of the hand and the hand geometry are compared to information on file for the intended subject. In some embodiments, the technologies to verify hand geometry information are known. In certain embodiments, such technologies include but are not limited to the devices, apparatus, and methods disclosed in U.S. Pat. Pub. Nos. 2016/0253658 and 2011/0175986, and U.S. Pat. Nos. 7,886,157, 9,336,634, 8,358,336, 8,279,042, 7,660,442, 7,616,784, 4,720,869, and 6,628,810, the disclosures of which are all incorporated by reference in their entireties.

In certain embodiments of the present invention, the biometric identifier is fingernail beds of the hand, where shapes, sizes and colors of the fingernail beds are used for biometric identification of the subject. The image(s)/video(s) captured by the camera 500 include fingernail beds of the hand and the fingernail beds are compared to information on file for the intended subject. In certain embodiments, the technologies to verify fingernail beds information are known. Such technologies include but are not limited to the devices, apparatus, and methods disclosed in U.S. Pat. Pub. No. 2007/0003114 and U.S. Pat. Nos. 6,631,199 and 5,751,835, the disclosures of which are all incorporated by reference in their entireties.

In certain embodiments, the identity of the subject being tested is verified by one biometric identifier. In certain embodiments, the identity of the subject being tested is verified by at least two biometric identifiers. In certain embodiments, the identity of the subject being tested is verified by at least three biometric identifiers. In certain embodiments, the identity of the subject being tested is verified by four or more biometric identifiers.

Figure 5:
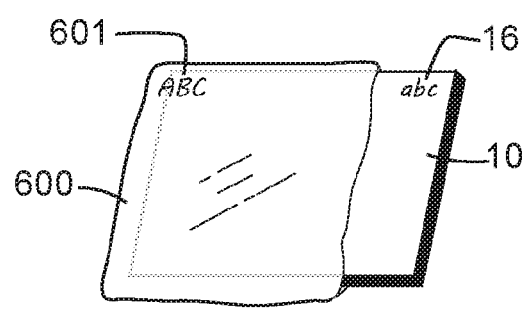
FIG. 5 illustrates an exemplary embodiment of the present invention, showing a package for the test plate.

FIG. 5 shows a perspective view of a package 600 and the test plate 10. In certain embodiments, the test plate 10 is sealed in a package 600 before the saliva test. For clarity purposes, FIG. 5 shows the package 600 and the test plate 10 when the test plate 10 is exposed. In certain embodiments, the package 600 is sealed before the saliva test and the test plate 10 is not accessed and/or seen without opening the package 600. In certain embodiments, the package 600 is opaque. It should also be noted that package 600 also contains other components of the present invention, such as but not limited to the cover plate 20, the camera 500, the processor, and the timing component. As indicated above, in certain embodiments, some or all of the components are integrated together. In certain embodiments, the integrated components would be contained in a single package.

As shown in FIG. 5, the package comprises a package identification (ID) 601, which can be any combination of numerical, alphabetical, symbolic or other characters and signs, as long as the package ID 601 can be used to identity the package 600 uniquely. In some embodiments, the device of the present invention uses the package ID 601 to identify the package 600.

In certain embodiments, the package ID 601 is paired with the plate ID 16 and the pairing is unknown to the subject. During the design/manufacturing of the device related to the saliva test, a design/manufacturing system generates pairs of the package ID 601 and the plate ID 16; such pairing is store by the system and it is not accessible or known by the subject. The agency/entity/professional administering the saliva test does or does not know the pairing. In other words, the subject only sees the test plate 10 (and the plate ID 16) for the first time after opening the package 600. It would impossible for the subject to prepare a fake plate beforehand because he/she does not know the plate ID 16.

In certain aspects, the present invention provides a device for authenticating a saliva sample from an intended subject being tested. The device comprises a test plate and a camera, wherein the test plate comprises a sample receiving area on its surface that receives a saliva sample from a subject that is being tested; wherein, during a sample deposition process in which the saliva sample is collected and deposited onto the sample receiving area of the test plate, the camera is configured to capture at least one image that simultaneously contains at least the following elements: (i) a plate ID that is configured to identify the test plate; (ii) one biometric identifier that identifies the subject being tested; and (iii) a saliva sample that is from the subject and that is deposited into the test plate, wherein the captured at least one image is used to determine that the saliva sample deposited into the test plate is from the intended subject.

In certain aspects, the present invention provides a device for authenticating a saliva sample from a subject being tested, comprising: a test plate and a camera, wherein the test plate comprises a sample receiving area on its surface that receives a saliva sample from an intended subject that is being tested; wherein, during a sample deposition process in which the saliva sample is collected and deposited onto the sample receiving area of the test plate, the camera is configured to capture a video that at least one frame of the video contains at least the following elements: (i) a plate ID that is configured to identify the test plate; (ii) one biometric identifier that identifies the subject being tested; and (iii) a saliva sample that is from the subject and that is deposited into the test plate; wherein the captured video is used to determine that the saliva sample deposited into the test plate is from the intended subject.

In certain aspects, the present invention provides a device for authenticating a saliva sample from a subject being tested, comprising: a test plate and a camera, wherein the test plate has: (i) a sample receiving area on its surface that receives a saliva sample from a subject that is being tested, wherein the sample is collected by a swab from the subject's mouth, and (ii) a plate ID which is a unique identifier of the plate; wherein the camera is configured to capture, during a sample deposition process in which the saliva sample on the swab is deposited onto the sample receiving area of the test plate: (i) one or more images that contain the face of the subject being tested when the saliva sample is being collected and the plate ID, and (ii) a video of a part or an entirety of the saliva sample deposition, wherein the video is used to determine that the saliva sample is deposited on the test plate; and wherein the image is used to determine that the subject being tested is the intended subject.

In certain aspects, the present invention provides a method of authenticating a saliva test, comprising: (a) providing a camera; (b) providing a test plate that has a sample receiving area on its surface; (c) collecting the saliva sample from the interior of the subject's mouth using a swab; (d) depositing the saliva sample onto the sample receiving area by touching the test plate with the swab; wherein (a') during the steps of (c)-(d), using the camera to capture at least one image or a video, wherein the at least one image or at least one frame of the video contains: (i) a plate ID that is configured to identify the test plate, (ii) one biometric identifier that identifies the subject being tested, and (iii) a saliva sample that is from the subject and that is deposited into the test plate; and (b') using the captured image or video to determine that the saliva sample deposited on the test plate is from the intended subject.

In certain aspects, the present invention provides a method of authenticating a saliva test, comprising: (a) providing a camera; (b) providing a test plate that has a sample receiving area on its surface; (c) collecting the saliva sample from the subject by passive drooling; (d) depositing the saliva sample onto the sample receiving area of the test plate; (e) during the steps of (c)-(d), using the camera to capture at least one image or a video, wherein the at least one image or at least one frame of the video contains: (i) a plate ID that is configured to identify the test plate, (ii) one biometric identifier that identifies the subject being tested, and (iii) the saliva sample that is from the subject and that is deposited into the test plate; and (f) using the captured image or video to determine that the saliva sample deposited on the test plate is from an intended subject.

In certain aspects, the present invention provides a method of authenticating a saliva test, comprising (a) providing a test plate that has a sample receiving area on its surface and a plate ID that uniquely identifies the plate; (b) providing a camera; (c) collecting the saliva sample from the interior of a subject's mouth using a swab; (d) depositing the saliva sample onto the sample receiving area by touching the test plate with the swab; and € during the deposition process (d), using the camera to capture: (i) one or more image of the saliva sample together with the face of the subject and the plate ID, and (ii) a video of a part or an entirety of the deposition process; and (f) using the captured image or video to determine that the saliva sample deposited on the test plate is from an intended subject.

In certain embodiments, the test cards are transparent (e.g. the QMAX card with two transparent plates), and in authenticating a saliva sample, the transparent test card is placed in the front of a camera, and the camera images, at the same time, both (a) the card and (b) a saliva taking process by a person through the transparent card. In certain embodiments, the saliva taking process also include a process of depositing a saliva from a swap on a test card and/or closing a cover (e.g. closing the plates in a QMAX device). In certain embodiments, the transparent test cards further comprises a card identification on the card that is visible to the camera. In certain embodiments, the transparent card ae visible in the camera. In certain embodiments, the camera imaging is a video, one or several still images, or a combination thereof.

In certain embodiments, the test device (e.g. the smartphone based test device) is configured to track the sample-to-test time which is the difference between the time of a saliva sample is taken and the time of the saliva sample being tested; and reject a test result if the sample-to-test time is longer than a threshold. In certain embodiments, a rejection threshold for the sample-to-test time is 2 sec, 5 sec, 10 sec, 20 sec, 20 sec, 30 sec, 60 sec, 80 sec, 100 sec, 120 sec, 150 sec, 200 sec, 250 sec, 300 sec, 360 sec, 420 sec, 500 sec, or a range of any two values. In certain embodiments, a preferred rejection threshold for the sample-to-test time is 2 sec, 5 sec, 10 sec, 20 sec, 20 sec, 30 sec, 60 sec, 80 sec, 100 sec, 120 sec, 150 sec, 180 sec, or a range of any two values. In certain embodiments, a preferred rejection threshold for the sample-to-test time is 2 sec, 5 sec, 10 sec, 20 sec, 20 sec, 30 sec, 60 sec, 80 sec, 100 sec, or a range of any two values.

The term "a rejection threshold for the sample-to-test time" is a time for the sample-to-test time, beyond which a test result for the saliva sample will be rejected.

In certain embodiments, the test card is a QMAX card, the camera used in authentication image the boundary of a saliva sample in the QMAX card in a closed configuration, and the camera used in assaying the saliva sample images the boundary of a saliva sample to be tested and compared it with the boundary during the saliva sample taking. If the two images match, the test results will be authenticated, otherwise, the test results will be rejected.

In certain embodiments, the biometric identifier is part or entirety of the face of the subject being tested. In certain embodiments, the biometric identifier is part or entirety of the iris of the subject being tested. In certain embodiments, the biometric identifier is part or entirety of the lip pattern of the subject being tested. In certain embodiments, the biometric identifier is one of the identifiers: face, iris, retina, lip pattern, ear geometry, skin tone, fingerprint, palmprint, hand geometry, vein pattern, sweat pore pattern, fingernail beds pattern or any combinations of thereof.

In certain embodiments, at least two biometric identifiers are used to determine that the subject being tested is the intended subject. In certain embodiments, at least three biometric identifiers are used to determine that the subject being tested is the intended subject.

In certain embodiments, the sample deposition process comprises collecting the saliva sample from the interior of the subject's mouth with a swab. In certain embodiments, the saliva sample is collected by saturating the swab under the tongue of the subject. In certain embodiments, the sample deposition process comprises touching the sample receiving area with the swab after collecting the saliva sample. In certain embodiments, the sample deposition process comprises collecting the saliva sample with passive drooling.

In certain embodiments, at least one image is recorded before the saliva sample touches the sample receiving area. In certain embodiments, at least one image is recorded after the saliva sample touches the sample receiving area. In certain embodiments, the images are recorded both before and after the saliva sample touches the sample receiving area.

In certain embodiments, the present devices further comprise hardware and software which are configured to process and analyze the images/videos. In certain embodiments, the hardware is a mobile phone and has local and/or long-distance communication capacities.

In certain embodiments, the positions of the test plate and the camera are configured to have the camera imaging the facial features of the subject and deposition of the saliva sample on the test plate in the same image frame.

In certain embodiments, the test plate is partial or completely transparent. In certain embodiments, the camera records the saliva deposition process from a side opposite to the sample receiving surface of the test plate. In certain embodiments, the camera images the biometric identifier of the subject and deposition of the saliva sample on the test plate in the same image frame.

In certain embodiments, the devices further comprise an optical fiber that is configured to image the face of the subject or the test plate by camera. The camera is a part of mobile phone. In certain embodiments, the mobile phone has a second camera for testing the test plate.

In certain embodiments, the test plate comprises a plate ID that is a is a sequence of digital and/or alphabetical characters, a 1-D barcode, a 2-D barcode, a QR code, a watermark, a waveform, or other machine-readable non-letter type code.

In certain embodiments, the camera is configured to capture an image or video that includes the plate identification. In certain embodiments, the camera is configured to capture images or videos of the saliva sample, the biometric identifier, the test plates, and the plate identification.

In certain embodiments, the test plate is sealed in a package before the saliva test; and the package comprises a package ID. In certain embodiments, the package ID is paired with the plate ID and the pairing is unknown to the subject being tested.

In certain embodiments, the device is used for health monitoring, mobile monitoring, crime monitoring, for insurance, for health, and/or for medication.

In certain embodiments, the test plate is configured to prevent sample switching after the deposition.

In certain embodiments, the camera is configured to capture the time points of: (i) collecting the saliva sample from the interior of the subject's mouth using a swab; and (ii) depositing the saliva sample by touching the test plate with the swab.

In certain embodiments, the devices comprise a processor, wherein the processor is configured to: (i) analyze the image of the biometric identifier captured by the camera; (ii) compare the biometric identifier with stored biometric identifier information of the subject; and (iii) determine whether the saliva sample provided in the saliva test is from the intended subject.

In certain embodiments, the prevention of sample switching comprises using of a CROF (Compressed Open Flow) test plate.

In certain embodiments, the test plate is part of a QMAX device (e.g. Q-card). The QMAX device and the Q-card are discussed below.

In certain embodiments, the present devices further comprise a cover plate that is configured to cover the test plate.

In certain embodiments, the present methods comprising: (a) analyzing the one or more images or video that include the biometric identifier; (b) comparing the biometric identifier to stored biometric information from the intended subject; and (c) determining whether the saliva provided in the saliva test is from the intended subject.

In certain embodiments, the present methods further comprising: (a) analyzing the video of the sample depositing process; and (b) determining whether the saliva sample is produced by the subject being tested.

In certain embodiments, the present methods comprise analyzing the image comprises evaluation of the geometry and/or shape of the saliva sample on the pricked finger.

In certain embodiments, the present methods comprise using the camera to capture a time point for depositing the saliva sample on the test plate.

In certain embodiments, the biometric information is stored in a local device, a cloud, or a combination thereof.

In certain embodiments, the comparison of the biometric identifier and the biometric information is conducted with a local device, a remote device, or a combination thereof.

Additional Examples of Present Inventions

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices/apparatus, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. No. 62/456,065, filed on Feb. 7, 2017, which is incorporated herein in its entirety for all purposes.

(2) Sample

The subject devices, apparatus, systems, and methods can be used to analyze any volume of the sample. Examples of the volumes include, but are not limited to, 10 mL or less, 5 mL or less, 3 mL or less, 1 microliter (µL, also "uL" herein) or less, 500 µL or less, 300 µL or less, 250 µL or less, 200 µL or less, 170 µL or less, 150 µL or less, 125 µL or less, 100 µL or less, 75 µL or less, 50 µL or less, 25 µL or less, 20 µL or less, 15 µL or less, 10 µL or less, 5 µL or less, 3 µL or less, 1 µL or less, 0.5 µL or less, 0.1 µL or less, 0.05 µL or less, 0.001 μL or less, 0.0005 μL or less, 0.0001 μL or less, 10 pL or less, 1 pL or less, or a range between any two of the values.

In certain embodiments, the volume of the sample includes, but is not limited to, 100 μL or less, 75 μL or less, 50 μL or less, 25 μL or less, 20 μL or less, 15 μL or less, 10 μL or less, 5 μL or less, 3 μL or less, 1 μL or less, 0.5 μL or less, 0.1 μL or less, 0.05 μL or less, 0.001 μL or less, 0.0005 μL or less, 0.0001 μL or less, 10 pL or less, 1 pL or less, or a range between any two of the values. In some embodiments, the volume of the sample includes, but is not limited to, about 10 μL or less, 5 μL or less, 3 μL or less, 1 μL or less, 0.5 μL or less, 0.1 μL or less, 0.05 μL or less, 0.001 μL or less, 0.0005 μL or less, 0.0001 μL or less, 10 pL or less, 1 pL or less, or a range between any two of the values.

In certain embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

In certain embodiments, the sample holder is configured to hold a fluidic sample. In certain embodiments, the sample holder is configured to compress at least part of the fluidic sample into a thin layer. In certain embodiments, the sample holder comprises structures that are configured to heat and/or cool the sample. In certain embodiments, the heating source provides electromagnetic waves that can be absorbed by certain structures in the sample holder to change the temperature of the sample. In certain embodiments, the signal sensor is configured to detect and/or measure a signal from the sample. In certain embodiments, the signal sensor is configured to detect and/or measure an analyte in the sample. In certain embodiments, the heat sink is configured to absorb heat from the sample holder and/or the heating source. In certain embodiments, the heat sink comprises a chamber that at least partly enclose the sample holder.

(3) Q-Card, Spacers and Uniform Sample Thickness

The devices/apparatus, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The term "open configuration" of the two plates in a QMAX process means a configuration in which the two plates are either partially or completely separated apart and the spacing between the plates is not regulated by the spacers The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample.

The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a QMAX card refers to the surface of the plate that touches the sample, while the other surface (that does not touch the sample) of the plate is termed "outer surface".

The term "height" or "thickness" of an object in a QMAX process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a QMAX process refers to, unless specifically stated, the area of the object that is parallel to a surface of the plate. For example, spacer area is the area of the spacer that is parallel to a surface of the plate.

The term of QMAX card refers the device that perform a QMAX (e.g. CROF) process on a sample, and have or not have a hinge that connect the two plates.

The term "QMAX card with a hinge and "QMAX card" are interchangeable.

The term "angle self-maintain", "angle self-maintaining", or "rotation angle self-maintaining" refers to the property of the hinge, which substantially maintains an angle between the two plates, after an external force that moves the plates from an initial angle into the angle is removed from the plates.

In using QMAX card, the two plates need to be open first for sample deposition. However, in some embodiments, the QMAX card from a package has the two plates are in contact each other (e.g. a close position), and to separate them is challenges, since one or both plates are very thing. To facilitate an opening of the QMAX card, opening notch or notches are created at the edges or corners of the first plate or both places, and, at the close position of the plates, a part of the second plate placed over the opening notch, hence in the notch of the first plate, the second plate can be lifted open without a blocking of the first plate.

In the QMAX assay platform, a QMAX card uses two plates to manipulate the shape of a sample into a thin layer (e.g. by compressing). In certain embodiments, the plate manipulation needs to change the relative position (termed: plate configuration) of the two plates several times by human hands or other external forces. There is a need to design the QMAX card to make the hand operation easy and fast.

In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers. In some embodiments, the average spacing between the two plates is more than 300 µm.

In a QMAX assay operation, an operator needs to first make the two plates to be in an open configuration ready for sample deposition, then deposit a sample on one or both of the plates, and finally close the plates into a close position. In certain embodiments, the two plates of a QMAX card are initially on top of each other and need to be separated to get into an open configuration for sample deposition. When one of the plates is a thin plastic film (175 um thick PMA), such separation can be difficult to perform by hand. The present invention intends to provide the devices and methods that make the operation of certain assays, such as the QMAX card assay, easy and fast.

In certain embodiments, the QMAX device comprises a hinge that connect two or more plates together, so that the plates can open and close in a similar fashion as a book. In some embodiments, the material of the hinge is such that the hinge can self-maintain the angle between the plates after adjustment. In some embodiments, the hinge is configured to maintain the QMAX card in the closed configuration, such that the entire QMAX card can be slide in and slide out a card slot without causing accidental separation of the two plates. In certain embodiments, the QMAX device comprises one or more hinges that can control the rotation of more than two plates.

In certain embodiments, the hinge is made from a metallic material that is selected from a group consisting of gold, silver, copper, aluminum, iron, tin, platinum, nickel, cobalt, alloys, or any combination of thereof. In certain embodiments, the hinge comprises a single layer, which is made from a polymer material, such as but not limited to plastics. The polymer material is selected from the group consisting of acrylate polymers, vinyl polymers, olefin polymers, cellulosic polymers, noncellulosic polymers, polyester polymers, Nylon, cyclic olefin copolymer (COC), poly(methyl methacrylate) (PMMB), polycarbonate (PC), cyclic olefin polymer (COP), liquid crystalline polymer (LCP), polyimide (PB), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFB), polydimethylsiloxane (PDMS), rubbers, or any combinations of thereof. In certain embodiments, the polymer material is selected from polystyrene, PMMB, PC, COC, COP, other plastic, or any combination thereof.

In essence, the term "spacers" or "stoppers" refer to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value.

The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes.

The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface.

In certain embodiments, human hands can be used to press the plates into a closed configuration; In some embodiments, human hands can be used to press the sample into a thin layer. The manners in which hand pressing is employed are described and/or summarized in PCT Application (designating U.S.) Nos. PCT/US2016/045437 filed on Aug. 10, 2016 and PCT/US0216/051775 filed on Sep. 14, 2016, and in U.S. Provisional Application Nos. 62/431,639 filed on Dec. 9, 2016, 62/456,287 filed on Feb. 8, 2017, 62/456,065 filed on Feb. 7, 2017, 62/456,504 filed on Feb. 8, 2017, and 62/460,062 filed on Feb. 16, 2017, which are all hereby incorporated by reference by their entireties.

In certain embodiments, human hand can be used to manipulate or handle the plates of the QMAX device. In certain embodiments, the human hand can be used to apply an imprecise force to compress the plates from an open configuration to a closed configuration. In certain embodiments, the human hand can be used to apply an imprecise force to achieve high level of uniformity in the thickness of the sample (e.g. less than 5%, 10%, 15%, or 20% variability).

(4) Hinges, Opening Notches, Recessed Edge and Sliders

The devices/apparatus, systems, and methods herein disclosed can include or use Q-cards for sample detection, analysis, and quantification. In certain embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/431,639, which was filed on Dec. 9, 2016, U.S. Provisional Application No. 62/456,065, which was filed on Feb. 7, 2017, U.S. Provisional Application Nos. 62/456,287 and 62/456,504, which was filed on Feb. 8, 2017, and U.S. Provisional Application No. 62/539,660, which was filed on Aug. 1, 2017, all of which applications are incorporated herein in their entireties for all purposes.

In certain embodiments, the QMAX device comprises opening mechanisms such as but not limited to notches on plate edges or strips attached to the plates, making is easier for a user to manipulate the positioning of the plates, such as but not limited to separating the plates of by hand.

In certain embodiments, the QMAX device comprises trenches on one or both of the plates. In certain embodiments, the trenches limit the flow of the sample on the plate.

(5) Q-Card and Adaptor

The devices/apparatus, systems, and methods herein disclosed can include or use Q-cards for sample detection, analysis, and quantification. In certain embodiments, the Q-card is used together with an adaptor that is configured to accommodate the Q-card and connect to a mobile device so that the sample in the Q-card can be imaged, analyzed, and/or measured by the mobile device. The structure, material, function, variation, dimension and connection of the Q-card, the adaptor, and the mobile are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application Nos. 62/460,075 and 62/459,920, which were filed on Feb. 16, 2017, all of which applications are incorporated herein in their entireties for all purposes.

In certain embodiments, the adaptor comprises a receptacle slot, which is configured to accommodate the QMAX device when the device is in a closed configuration. In certain embodiments, the QMAX device has a sample deposited therein and the adaptor can be connected to a mobile device (e.g. a smartphone) so that the sample can be read by the mobile device. In certain embodiments, the mobile device can detect and/or analyze a signal from the sample. In certain embodiments, the mobile device can capture images of the sample when the sample is in the QMAX device and positioned in the field of view (FOV) of a camera, which in certain embodiments, is part of the mobile device.

In certain embodiments, the adaptor comprises optical components, which are configured to enhance, magnify, and/or optimize the production of the signal from the sample. In some embodiments, the optical components include parts that are configured to enhance, magnify, and/or optimize illumination provided to the sample. In certain embodiments, the illumination is provided by a light source that is part of the mobile device. In certain embodiments, the optical components include parts that are configured to enhance, magnify, and/or optimize a signal from the sample.

(6) Smartphone Detection System

The devices/apparatus, systems, and methods herein disclosed can include or use Q-cards for sample detection, analysis, and quantification. In certain embodiments, the Q-card is used together with an adaptor that can connect the Q-card with a smartphone detection system. In certain embodiments, the smartphone comprises a camera and/or an illumination source The smartphone detection system, as well the associated hardware and software are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application Nos. 62/460,075 and 62/459,920, which were filed on Feb. 16, 2017, all of which applications are incorporated herein in their entireties for all purposes.

In certain embodiments, the smartphone comprises a camera, which can be used to capture images or the sample when the sample is positioned in the field of view of the camera (e.g. by an adaptor). In certain embodiments, the camera includes one set of lenses (e.g. as in iPhone™ 6). In certain embodiments, the camera includes at least two sets of lenses (e.g. as in iPhone™ 7). In some embodiments, the smartphone comprises a camera, but the camera is not used for image capturing.

In some embodiments, the smartphone comprises a light source such as but not limited to LED (light emitting diode). In certain embodiments, the light source is used to provide illumination to the sample when the sample is positioned in the field of view of the camera (e.g. by an adaptor). In some embodiments, the light from the light source is enhanced, magnified, altered, and/or optimized by optical components of the adaptor.

In some embodiments, the smartphone comprises a processor that is configured to process the information from the sample. The smartphone includes software instructions that, when executed by the processor, can enhance, magnify, and/or optimize the signals (e.g. images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In some embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof.

In some embodiments, the smartphone is an iPhone™, an Android™ phone, or a Windows™ phone.

(7) Detection Methods

The devices/apparatus, systems, and methods herein disclosed can include or be used in various types of detection methods. The detection methods are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287, 62/456,528, 62/456,631, 62/456522, 62/456,598, 62/456,603, and 62/456,628, which were filed on Feb. 8, 2017, U.S. Provisional Application Nos. 62/459, 276, 62/456,904, 62/457,075, and 62/457,009, which were filed on Feb. 9, 2017, and U.S. Provisional Application Nos. 62/459,303, 62/459,337, and 62/459,598, which were filed on Feb. 15, 2017, and U.S. Provisional Application Nos. 62/460,083, 62/460,076, which were filed on Feb. 16, 2017, all of which applications are incorporated herein in their entireties for all purposes.

(8) Labels, Capture Accent and Detection Accent

The devices/apparatus, systems, and methods herein disclosed can employ various types of labels, capture agents, and detection agents that are used for analytes detection. The labels are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In certain embodiments, the label is optically detectable, such as but not limited to a fluorescence label. In some embodiments, the labels include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-di methylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)amino- -fluorescein (DTAF), 2',7'dimethoxy-4'5'-dichloro-6-carboxyfluorescein (JOE), fluorescein, fluorescein isothiocyanate, QFITC, (XRITC); fluorescamine; 1R144; 1R1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAM RA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalol cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from Aequoria victoria or a derivative thereof, e.g., a "humanized" derivative such as Enhanced GFP; a GFP from another species such as Renilla reniformis, Renilla mulleri, or Ptilosarcus guernyi; "humanized" recombinant GFP (hrGFP); any of a variety of fluorescent and colored proteins from Anthozoan species; combinations thereof; and the like.

In certain embodiments, the QMAX device can contain a plurality of capture agents and/or detection agents that each bind to a biomarker selected from Tables B1, B2, B3 and/or B7 in U.S. Provisional Application No. 62/234,538 and/or PCT Application No. PCT/US2016/054025, wherein the reading step d) includes obtaining a measure of the amount of the plurality of biomarkers in the sample, and wherein the amount of the plurality of biomarkers in the sample is diagnostic of a disease or condition.

In certain embodiments the capture agent and/or detection agents can be an antibody epitope and the biomarker can be an antibody that binds to the antibody epitope. In certain embodiments, the antibody epitope includes a biomolecule, or a fragment thereof, selected from Tables B4, B5 or B6 in U.S. Provisional Application No. 62/234,538 and/or PCT Application No. PCT/US2016/054025. In certain embodiments, the antibody epitope includes an allergen, or a fragment thereof, selected from Table B5. In certain embodiments, the antibody epitope includes an infectious agent-derived biomolecule, or a fragment thereof, selected from Table B6 in U.S. Provisional Application No. 62/234,538 and/or PCT Application No. PCT/US2016/054025.

In certain embodiments, the QMAX device can contain a plurality of antibody epitopes selected from Tables B4, B5 and/or B6 in U.S. Provisional Application No. 62/234,538 and/or PCT Application No. PCT/US2016/054025, wherein the reading step d) includes obtaining a measure of the amount of a plurality of epitope-binding antibodies in the sample, and wherein the amount of the plurality of epitope-binding antibodies in the sample is diagnostic of a disease or condition.

(9) Analytes

The devices/apparatus, systems, and methods herein disclosed can be applied to manipulation and detection of various types of analytes (including biomarkers). The analyte include, but not limited, to proteins, cells, small molecules, nuclear acid, tissues, and nanoparticles. The analytes are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The devices, apparatus, systems, and methods herein disclosed can be used for the detection, purification and/or quantification of various analytes. In some embodiments, the analytes are biomarkers that associated with various diseases. In some embodiments, the analytes and/or biomarkers are indicative of the presence, severity, and/or stage of the diseases. The analytes, biomarkers, and/or diseases that can be detected and/or measured with the devices, apparatus, systems, and/or method of the present invention include the analytes, biomarkers, and/or diseases listed, described, and/or summarized in PCT Application (designating U.S.) Nos. PCT/US2016/045437 filed on Aug. 10, 2016, and PCT Application No. PCT/US2016/054025 filed on Sep. 27, 2016, and U.S. Provisional Application Nos. 62/234,538 filed on Sep. 29, 2015, 62/233,885 filed on Sep. 28, 2015, 62/293,188 filed on Feb. 9, 2016, and 62/305,123 filed on Mar. 8, 2016, which are all hereby incorporated by reference by their entireties. For example, the devices, apparatus, systems, and methods herein disclosed can be used in (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

In certain embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food. In certain preferred embodiments, the sample is a saliva.

In certain embodiments, the sample can be a diagnostic sample obtained from a subject, the analyte can be a biomarker, and the measured the amount of the analyte in the sample can be diagnostic of a disease or a condition.

In certain embodiments, the devices, apparatus, systems, and methods in the present invention can further include diagnosing the subject based on information including the measured amount of the biomarker in the sample. In some cases, the diagnosing step includes sending data containing the measured amount of the biomarker to a remote location and receiving a diagnosis based on information including the measurement from the remote location.

In certain embodiments, the biomarker can be selected from Tables B1, 2, 3 or 7 as disclosed in U.S. Provisional Application Nos. 62/234,538, 62/293,188, and/or 62/305,123, and/or PCT Application No. PCT/US2016/054,025, which are all incorporated in their entireties for all purposes. In some instances, the biomarker is a protein selected from Tables B1, 2, or 3. In some instances, the biomarker is a nucleic acid selected from Tables B2, 3 or 7. In some instances, the biomarker is an infectious agent-derived biomarker selected from Table B2. In some instances, the biomarker is a microRNA (miRNA) selected from Table B7.

In certain embodiments, the applying step b) can include isolating miRNA from the sample to generate an isolated miRNA sample, and applying the isolated miRNA sample to the disk-coupled dots-on-pillar antenna (QMAX device) array.

In certain embodiments, the QMAX device can contain a plurality of capture agents that each bind to a biomarker selected from Tables B1, B2, B3 and/or B7, wherein the reading step d) includes obtaining a measure of the amount of the plurality of biomarkers in the sample, and wherein the amount of the plurality of biomarkers in the sample is diagnostic of a disease or condition.

In certain embodiments, the capture agent can be an antibody epitope and the biomarker can be an antibody that binds to the antibody epitope. In some embodiments, the antibody epitope includes a biomolecule, or a fragment thereof, selected from Tables B4, B5 or B6. In some embodiments, the antibody epitope includes an allergen, or a fragment thereof, selected from Table B5. In certain embodiments, the antibody epitope includes an infectious agent-derived biomolecule, or a fragment thereof, selected from Table B6.

In certain embodiments, the QMAX device can contain a plurality of antibody epitopes selected from Tables B4, B5 and/or B6, wherein the reading step d) includes obtaining a measure of the amount of a plurality of epitope-binding antibodies in the sample, and wherein the amount of the plurality of epitope-binding antibodies in the sample is diagnostic of a disease or condition.

In certain embodiments, the sample can be an environmental sample, and wherein the analyte can be an environmental marker. In some embodiments, the environmental marker is selected from Table B8 in U.S. Provisional Application No. 62/234,538 and/or PCT Application No. PCT/US2016/054025.

In certain embodiments, the method can include receiving or providing a report that indicates the safety or harmfulness for a subject to be exposed to the environment from which the sample was obtained.

In certain embodiments, the method can include sending data containing the measured amount of the environmental marker to a remote location and receiving a report that indicates the safety or harmfulness for a subject to be exposed to the environment from which the sample was obtained.

In certain embodiments, the QMAX device array can include a plurality of capture agents that each bind to an environmental marker selected from Table B8, and wherein the reading step d) can include obtaining a measure of the amount of the plurality of environmental markers in the sample.

In certain embodiments, the sample can be a foodstuff sample, wherein the analyte can be a foodstuff marker, and wherein the amount of the foodstuff marker in the sample can correlate with safety of the foodstuff for consumption. In some embodiments, the foodstuff marker is selected from Table B9.

In certain embodiments, the method can include receiving or providing a report that indicates the safety or harmfulness for a subject to consume the foodstuff from which the sample is obtained.

In certain embodiments, the method can include sending data containing the measured amount of the foodstuff marker to a remote location and receiving a report that indicates the safety or harmfulness for a subject to consume the foodstuff from which the sample is obtained.

In certain embodiments, the devices, apparatus, systems, and methods herein disclosed can include a plurality of capture agents that each binds to a foodstuff marker selected from Table B9 from in U.S. Provisional Application No. 62/234,538 and PCT Application No. PCT/US2016/054025, wherein the obtaining can include obtaining a measure of the amount of the plurality of foodstuff markers in the sample, and wherein the amount of the plurality of foodstuff marker in the sample can correlate with safety of the foodstuff for consumption.

Also provided herein are kits that find use in practicing the devices, systems and methods in the present invention.

The amount of sample can be about a drop of a sample. The amount of sample can be the amount collected from a pricked finger or fingerstick. The amount of sample can be the amount collected from a microneedle or a venous draw.

A sample can be used without further processing after obtaining it from the source, or can be processed, e.g., to enrich for an analyte of interest, remove large particulate matter, dissolve or resuspend a solid sample, etc.

A sample can be collected at one time, or at a plurality of times. Samples collected over time can be aggregated and/or processed (by applying to a QMAX device and obtaining a measurement of the amount of analyte in the sample, as described herein) individually. In some instances, measurements obtained over time can be aggregated and can be useful for longitudinal analysis over time to facilitate screening, diagnosis, treatment, and/or disease prevention.

Washing the QMAX device to remove unbound sample components can be done in any convenient manner, as described above. In certain embodiments, the surface of the QMAX device is washed using binding buffer to remove unbound sample components.

Detectable labeling of the analyte can be done by any convenient method. The analyte can be labeled directly or indirectly. In direct labeling, the analyte in the sample is labeled before the sample is applied to the QMAX device. In indirect labeling, an unlabeled analyte in a sample is labeled after the sample is applied to the QMAX device to capture the unlabeled analyte, as described below.

(10) Applications

The devices/apparatus, systems, and methods herein disclosed can be used for various applications (fields and samples). The applications are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In certain embodiments, the devices, apparatus, systems, and methods herein disclosed are used in a variety of different application in various field, wherein determination of the presence or absence, quantification, and/or amplification of one or more analytes in a sample are desired. For example, in certain embodiments the subject devices, apparatus, systems, and methods are used in the detection of proteins, peptides, nucleic acids, synthetic compounds, inorganic compounds, organic compounds, bacteria, virus, cells, tissues, nanoparticles, and other molecules, compounds, mixtures and substances thereof. The various fields in which the subject devices, apparatus, systems, and methods can be used include, but are not limited to: diagnostics, management, and/or prevention of human diseases and conditions, diagnostics, management, and/or prevention of veterinary diseases and conditions, diagnostics, management, and/or prevention of plant diseases and conditions, agricultural uses, veterinary uses, food testing, environments testing and decontamination, drug testing and prevention, and others.

The applications of the present invention include, but are not limited to: (a) the detection, purification, quantification, and/or amplification of chemical compounds or biomolecules that correlates with certain diseases, or certain stages of the diseases, e.g., infectious and parasitic disease, injuries, cardiovascular disease, cancer, mental disorders, neuropsychiatric disorders and organic diseases, e.g., pulmonary diseases, renal diseases, (b) the detection, purification, quantification, and/or amplification of cells and/or microorganism, e.g., virus, fungus and bacteria from the environment, e.g., water, soil, or biological samples, e.g., tissues, bodily fluids, (c) the detection, quantification of chemical compounds or biological samples that pose hazard to food safety, human health, or national security, e.g. toxic waste, anthrax, (d) the detection and quantification of vital parameters in medical or physiological monitor, e.g., glucose, blood oxygen level, total blood count, (e) the detection and quantification of specific DNA or RNA from biological samples, e.g., cells, viruses, bodily fluids, (f) the sequencing and comparing of genetic sequences in DNA in the chromosomes and mitochondria for genome analysis or (g) the detection and quantification of reaction products, e.g., during synthesis or purification of pharmaceuticals.

In certain embodiments, the subject devices, apparatus, systems, and methods are used in the detection of nucleic acids, proteins, or other molecules or compounds in a sample. In certain embodiments, the devices, apparatus, systems, and methods are used in the rapid, clinical detection and/or quantification of one or more, two or more, or three or more disease biomarkers in a biological sample, e.g., as being employed in the diagnosis, prevention, and/or management of a disease condition in a subject. In certain embodiments, the devices, apparatus, systems, and methods are used in the detection and/or quantification of one or more, two or more, or three or more environmental markers in an environmental sample, e.g. sample obtained from a river, ocean, lake, rain, snow, sewage, sewage processing runoff, agricultural runoff, industrial runoff, tap water or drinking water. In certain embodiments, the devices, apparatus, systems, and methods are used in the detection and/or quantification of one or more, two or more, or three or more foodstuff marks from a food sample obtained from tap water, drinking water, prepared food, processed food or raw food.

In certain embodiments, the subject device is part of a microfluidic device. In some embodiments, the subject devices, apparatus, systems, and methods are used to detect a fluorescence or luminescence signal. In certain embodiments, the subject devices, apparatus, systems, and methods include, or are used together with, a communication device, such as but not limited to: mobile phones, tablet computers and laptop computers. In certain embodiments, the subject devices, apparatus, systems, and methods include, or are used together with, an identifier, such as but not limited to an optical barcode, a radio frequency ID tag, or combinations thereof.

(11) Dimensions

The devices, apparatus, systems, and methods herein disclosed can include or use a QMAX device, which can comprise plates and spacers. In some embodiments, the dimension of the individual components of the QMAX device and its adaptor are listed, described and/or summarized in PCT Application (designating U.S.) No. PCT/US2016/045437 filed on Aug. 10, 2016, and U.S. Provisional Application Nos. 62/431,639 filed on Dec. 9, 2016 and 62/456,287 filed on Feb. 8, 2017, which are all hereby incorporated by reference by their entireties.

In certain embodiments, the dimensions are listed in Tables 1-5 below:

TABLE 1

| | Plates | |
|---|---|---|
| Parameters | Embodiments | Preferred Embodiments |
| Shape | Round, ellipse, rectangle, triangle, polygonal, ring-shaped, or any superposition of these shapes; the two (or more) plates of the QMAX card can have the same size and/or shape, or different size and/or shape | At least one of the two (or more) plates of the QMAX card has round corners for user safety concerns, wherein the round corners have a diameter of 100 μm or less, 200 μm or less, 500 μm or less, 1 mm or less, 2 mm or less, 5 mm or less, 10 mm or less, 50 mm or less, or in a range between any two of the values. |
| Thickness | The average thickness for at least one of the plates is 2 nm or less, 10 nm or less, 100 nm or less, 200 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, 20 mm or less, 50 mm or less, 100 mm or less, 500 mm or less, or in a range between any two of these values | For at least one of the plates is in the range of 0.5 to 1.5 mm; around 1 mm; in the range of 0.15 to 0.2 mm; or around 0.175 mm |
| Lateral Area | For at least one of the plate is 1 mm$^2$ (square millimeter) or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, 500 cm$^2$ or less, 1000 cm$^2$ or less, 5,000 cm$^2$ or less, 10,000 cm$^2$ or less, 10,000 cm$^2$ or less, or in a range between any two of these values | For at least one plate of the QMAX card is in the range of 500 to 1000 mm$^2$; or around 750 mm$^2$ |
| Lateral Linear Dimension (width, length, or diameter, etc.) | For at least one of the plates of the QMAX card is 1 mm or less, 5 mm or less, 10 mm or less, 15 mm or less, 20 mm or less, 25 mm or less, 30 mm or less, 35 mm or less, 40 mm or less, 45 mm or less, 50 mm or less, 100 mm or less, 200 mm or less, 500 mm or less, 1000 mm or less, 5000 mm or less, or in a range between any two of these values | For at least one plate of the QMAX card is in the range of 20 to 30 mm; or around 24 mm |
| Recess width | 1 μm or less, 10 μm or less, 20 μm or less, 30 μm or less, 40 μm or less, 50 μm or less, 100 μm or less, 200 μm or less, 300 μm or less, 400 μm or less, 500 μm or less, 7,500 μm or less, 1 mm or less, 5 mm or less, 10 mm or less, 100 mm or less, or 1,000 mm or less, or in a range between any two of these values. | In the range of 1 mm to 10 mm; Or About 5 mm |

TABLE 2

| | Hinge | |
|---|---|---|
| Parameters | Embodiments | Preferred Embodiments |
| Number | 1, 2, 3, 4, 5, or more | 1 or 2 |
| Length of Hinge Joint | 1 mm or less, 2 mm or less, 3 mm or less, 4 mm or less, 5 mm or less, 10 mm or less, 15 mm or less, 20 mm or less, 25 mm or less, 30 mm or less, 40 mm or less, 50 mm or less, 100 mm or less, 200 mm or less, or 500 mm or less, or in a range between any two of these values | In the range of 5 mm to 30 mm. |
| Ratio (hinge joint length vs. aligning plate edge length | 1.5 or less, 1 or less, 0.9 or less, 0.8 or less, 0.7 or less, 0.6 or less, 0.5 or less, 0.4 or less, 0.3 or less, 0.2 or less, 0.1 or less, 0.05 or less or in a range between any two of these values | In the range of 0.2 to 1; or about 1 |
| Area | 1 $mm^2$ or less, 5 $mm^2$ or less, 10 $mm^2$ or less, 20 $mm^2$ or less, 30 $mm^2$ or less, 40 $mm^2$ or less, 50 $mm^2$ or less, 100 $mm^2$ or less, 200 $mm^2$ or less, 500 $mm^2$ or less, or in a range between any of the two values | In the range of 20 to 200 $mm^2$; or about 120 $mm^2$ |
| Ratio (hinge area vs. plate area) | 1 or less, 0.9 or less, 0.8 or less, 0.7 or less, 0.6 or less, 0.5 or less, 0.4 or less, 0.3 or less, 0.2 or less 0.1 or less, 0.05 or less, 0.01 or less or in a range between any two of these values | In the range of 0.05 to 0.2, around 0.15 |
| Max. Open Degree | 15 or less, 30 or less, 45 or less, 60 or less, 75 or less, 90 or less, 105 or less, 120 or less, 135 or less, 150 or less, 165 or less, 180 or less, 195 or less, 210 or less, 225 or less, 240 or less, 255 or less, 270 or less, 285 or less, 300 or less, 315 or less, 330 or less, 345 or less or 360 or less degrees, or in a range between any two of these values | In the range of 90 to 180 degrees |
| No. of Layers | 1, 2, 3, 4, 5, or more | 1 or 2 |
| Layer thickness | 0.1 μm or less, 1 μm or less, 2 μm or less, 3 μm or less, 5 μm or less, 10 μm or less, 20 μm or less, 30 μm or less, 50 μm or less, 100 μm or less, 200 μm or less, 300 μm or less, 500 μm or less, 1 mm or less, 2 mm or less, and a range between any two of these values | In the range of 20 μm to 1 mm; or Around 50 μm |
| Angle-maintaining | Limiting the angle adjustment with no more than ±90, ±45, ±30, ±25, ±20, ±15, ±10, ±8, ±6, ±5, ±4, ±3, ±2, or ±1, or in a range between any two of these values | No more than ±2 |

TABLE 3

| | Notch | |
|---|---|---|
| Parameters | Embodiments | Preferred Embodiments |
| Number | 1, 2, 3, 4, 5, or more | 1 or 2 |
| Shape | Round, ellipse, rectangle, triangle, polygon, ring-shaped, or any superposition or portion of these shapes. | Part of a circle |
| Positioning | Any location along any edge except the hinge edge, or any corner joint by non-hinge edges | |
| Lateral Linear Dimension (Length along the edge, radius, etc.) | 1 mm or less, 2.5 mm or less, 5 mm or less, 10 mm or less, 15 mm or less, 20 mm or less, 25 mm or less, 30 mm or less, 40 mm or less, 50 mm or less, or in a range between any two of these values | In the range of 5 mm to 15 mm; or about 10 mm |
| Area | 1 $mm^2$ (square millimeter) or less, 10 $mm^2$ or less, 25 $mm^2$ or less, 50 $mm^2$ or less, 75 $mm^2$ or less or in a range between any two of these values. | In the range of 10 to 150 $mm^2$; or about 50 $mm^2$ |

TABLE 4

| | Trench | |
|---|---|---|
| Parameters | Embodiments | Preferred Embodiments |
| Number | 1, 2, 3, 4, 5, or more | 1 or 2 |
| Shape | Closed (round, ellipse, rectangle, triangle, polygon, ring-shaped, or any superposition or portion of these shapes) or open-ended (straight | |

TABLE 4-continued

Trench

| Parameters | Embodiments | Preferred Embodiments |
|---|---|---|
| Length | line, curved line, arc, branched tree, or any other shape with open endings); 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, or in a range between any two of these values | |
| Cross-sectional Area | 0.001 mm$^2$ or less, 0.005 mm$^2$ or less, 0.01 mm$^2$ or less, 0.05 mm$^2$ or less, 0.1 mm$^2$ or less, 0.5 mm$^2$ or less, 1 mm$^2$ or less, 2 mm$^2$ or less, 5 mm$^2$ or less, 10 mm$^2$ or less, 20 mm$^2$ or less, or in a range between any two of these values. | |
| Volume | 0.1 μL or more, 0.5 μL or more, 1 μL or more, 2 μL or more, 5 μL or more, 10 μL or more, 30 μL or more, 50 μL or more, 100 μL or more, 500 μL or more, 1 mL or more, or in a range between any two of these values | In the range of 1 μL to 20 μL; or About 5 μL |

TABLE 5

Receptacle Slot

| Parameters | Embodiments | Preferred Embodiments |
|---|---|---|
| Shape of receiving area | Round, ellipse, rectangle, triangle, polygon, ring-shaped, or any superposition of these shapes; | |
| Difference between sliding track gap size and card thickness | 100 nm, 500 nm, 1 μm, 2 μm, 5 μm, 10 μm, 50 μm, 100 μm, 300 μm, 500 μm, 1 mm, 2 mm, 5 mm, 1 cm, or in a range between any two of the values. | In the range of 50 to 300 μm; or about 75 μm |
| Difference between receiving area and card area | 1 mm$^2$ (square millimeter) or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, or in a range between any of the two values. | |

(12) Cloud

The devices/apparatus, systems, and methods herein disclosed can employ cloud technology for data transfer, storage, and/or analysis. The related cloud technologies are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In certain embodiments, the cloud storage and computing technologies can involve a cloud database. Merely by way of example, the cloud platform can include a private cloud, a public cloud, a hybrid cloud, a community cloud, a distributed cloud, an inter-cloud, a multi-cloud, or the like, or any combination thereof. In some embodiments, the mobile device (e.g. smartphone) can be connected to the cloud through any type of network, including a local area network (LAN) or a wide area network (WAN).

In certain embodiments, the data (e.g. images of the sample) related to the sample is sent to the cloud without processing by the mobile device and further analysis can be conducted remotely. In certain embodiments, the data related to the sample is processed by the mobile device and the results are sent to the cloud. In certain embodiments, both the raw data and the results are transmitted to the cloud.

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entities in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entities so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

The practice of various embodiments of the present disclosure employs, unless otherwise indicated, conventional techniques of immunology, biochemistry, chemistry, molecular biology, microbiology, cell biology, genomics and recombinant DNA, which are within the skill of the art. See Green and Sambrook, MOLECULAR CLONING: A LABORATORY MANUAL, 4th edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

The foregoing and other objects, aspects, features, and advantages of the present invention will become more apparent from the following description and from the claims. Variations, modifications, and other implementations of what is described herein will occur to those of ordinary skill in the art without departing from the spirit and the scope of the invention as claimed. Accordingly, the present invention is to be defined not by the preceding illustrative description but instead by the spirit and scope of the following claims.

What is claimed is:

1. A device for authenticating a saliva sample from a subject being tested, comprising:
   (a) a test plate, a cover plate and spacers, wherein:
      (i) the test plate and the cover plate movable relative to each other into different configurations, including an open configuration and a closed configuration;
      (ii) the spacers are fixed on one of the cover and test plates;
      (iii) the test plate and the cover plate comprises, respectively, a sample receiving area on its surface that receives the saliva sample from a subject being tested; and
      (iv) one or both of the cover and test plates are transparent; and
   (b) a first camera, wherein, during a sample deposition process in which a saliva sample is collected and deposited onto the sample receiving area of the test plate, the first camera is configured to capture a first image that contains at least the following:
      i. a plate ID that is configured to identify the test plate,
      ii. a biometric identifier that identifies the subject being tested, and
      iii. a saliva sample that is from the subject being tested and that is deposited onto the test plate,
      wherein the first image comprises an image of the geometry and/or shape of a saliva sample when the test and cover plates are in the closed configuration; and
   (c) a second camera or the first camera that images, during an assaying of the saliva samples, capture a second image of the geometry and/or shape of a saliva sample when the test and cover plates are in the closed configuration;
wherein the first image and the second image are compared to authenticate that the deposited saliva sample is from an intended subject;
wherein the authentication uses a match of the geometry and/or shape of a saliva sample in the first image and the second image;
wherein, in the open configuration, the cover and test plates are either partially or completely separated apart, and the spacing between the cover and test plates is not regulated by the spacers; and
wherein in the closed configuration, the cover and test plates are facing each other and confine the saliva sample between the cover and test plates, making at least part of the saliva sample into a thin layer of a uniform thickness, wherein the uniform thickness is regulated by the plates and the spacers.

2. A method of authenticating a saliva test, comprising:
(a) providing a camera;
(b) providing a test plate that has a sample receiving area on its surface;
(c) collecting a saliva sample from interior of an intended subject's mouth using a swab;
(d) depositing the saliva sample onto the sample receiving area by touching the test plate with the swab;
(e) during the steps of (c)-(d), using the camera to capture at least an image or a video, wherein the image or the video contains:
  i. a plate ID that is configured to identify the test plate,
  ii. a biometric identifier that identifies the subject being tested, and
  iii. a saliva sample that is from the subject and that is deposited onto the test plate; and
wherein the image or the video contains the geometry and/or shape of the saliva sample on the test plate and
(f) using the captured image or video to authenticate that the saliva sample deposited onto the test plate is from an intended subject, wherein the authentication comprises evaluating the geometry and/or shape of the saliva sample on the test plate.

3. A method of authenticating a saliva test, comprising:
(a) providing a camera;
(b) providing the device of claim 1;
(c) collecting a saliva sample from a subject;
(d) depositing the saliva sample onto the sample receiving area of the test plate;
(e) during the steps of (c)-(d), using the first camera to capture at least an image or a video, wherein the image or the video contains:
  i. a plate ID that is configured to identify the test plate,
  ii. one biometric identifier that identifies the subject being tested, and
  iii. the geometry and/or shape of the saliva sample that is from the subject being tested and that is deposited into the test plate;
(f) using the captured image or video to authenticate that the saliva sample deposited onto the test plate is from an intended subject, wherein the authentication comprises evaluating the geometry and/or shape of the saliva sample on the test plate.

4. The device of claim 1, wherein the test card is transparent and is positioned in the front of the camera, so that the camera images, at the same time, (i) the card and (ii), through the card, the saliva taking process.

5. The device of claim 1, further comprising a rejection threshold for the sample-to-test time is 2 sec, 5 sec, 10 sec, 20 sec, 30 sec, 60 sec, 80 sec, 100 sec, or a range of any two values, wherein any results with a sample to test time is larger than the threshold is rejected.

6. The device of claim 1, wherein the biometric identifier is part or entirety of the face of the intended subject being tested; part or entirety of the iris of the subject being tested; or part or entirety of the lip pattern of the subject being tested.

7. The device of claim 1, wherein the biometric identifier is one of the identifiers: face, iris, retina, lip pattern, ear geometry, skin tone, fingerprint, palmprint, hand geometry, vein pattern, sweat pore pattern, fingernail beds pattern or any combinations of thereof.

8. The device of claim 1, wherein the at least two biometric identifiers are used to authenticate that the subject being tested is the intended subject.

9. The method of claim 2, wherein the images are recorded both before and after the saliva sample touches the sample receiving area.

10. The device of claim 1, wherein the positions of the test plate and the camera are configured to have the camera imaging the facial features of the subject being tested and deposition of the saliva sample on the test plate in the same image frame.

11. The device of claim 1, wherein:
i. the test plate is partial or completely transparent,
ii. the camera records the saliva deposition process from a side opposite to the sample receiving surface of the test plate, and
iii. the camera images the biometric identifier of the subject being tested and deposition of the saliva sample on the test plate in the same image frame.

12. The device of claim 1, wherein the device further comprises an optical fiber that is configured to image the face of the subject being tested or the test plate by camera.

13. The device of claim 1, wherein the camera is a part of mobile phone.

14. The device of claim 1, wherein the test plate comprises a plate ID that is a is a sequence of digital and/or alphabetical characters, a 1-D barcode, a 2-D barcode, a QR code, a watermark, a waveform, or other machine-readable non-letter type code.

15. The method of claim 2, wherein the device is used for health monitoring, mobile monitoring, crime monitoring, for insurance, for health, and/or for medication.

16. The method of claim 2, wherein the camera is further configured to capture the time points of:
i. collecting the saliva sample from the interior of the subject's mouth using a swab; and
ii. depositing the saliva sample by touching the test plate with the swab.

17. The method of claim 2, further comprising:
(a) analyzing the one or more images or video that include the biometric identifier;
(b) comparing the biometric identifier to stored biometric information from the intended subject; and
(c) determining whether the saliva provided in the saliva test is from the intended subject.

18. The method of claim 2, further comprising:
(a) analyzing the video of the sample depositing process; and
(b) determining whether the saliva sample is produced by the subject being tested.

19. The method of claim 2, wherein the comparison of the biometric identifier and the biometric information is conducted with a local device, a remote device, or a combination thereof.

* * * * *